(12) United States Patent
Nakamura

(10) Patent No.: US 6,606,113 B2
(45) Date of Patent: *Aug. 12, 2003

(54) STEREOSCOPIC ENDOCSOPE SYSTEM AND TV IMAGING SYSTEM FOR ENDOSCOPE

(75) Inventor: Shinichi Nakamura, Hachioji (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/682,562
(22) PCT Filed: May 21, 1996
(86) PCT No.: PCT/JP96/01343
§ 371 (c)(1),
(2), (4) Date: Jul. 25, 1996
(87) PCT Pub. No.: WO96/37796
PCT Pub. Date: Nov. 28, 1996

(65) Prior Publication Data
US 2001/0012053 A1 Aug. 9, 2001

(51) Int. Cl.⁷ .............................. H04N 15/00; A61B 1/06
(52) U.S. Cl. .......................... 348/45; 600/160; 600/166
(58) Field of Search .......................... 348/45, 68, 139, 348/195, 197, 65, 56; 600/160, 166, 117, 101; 359/377; H04N 7/18

(56) References Cited

U.S. PATENT DOCUMENTS

| 4,363,629 A | * 12/1982 | Lang et al. | 359/377 |
| 4,862,873 A | * 9/1989 | Yajima et al. | 348/45 |
| 4,884,876 A | * 12/1989 | Lipton et al. | 348/56 |
| 5,436,655 A | * 7/1995 | Hiyama et al. | 348/45 |
| 5,557,454 A | * 9/1996 | Takahashi | 348/45 |
| 5,588,948 A | * 12/1996 | Takahashi et al. | 348/45 |
| 5,613,936 A | * 3/1997 | Czarnek et al. | 600/166 |
| 5,743,846 A | * 4/1998 | Takahashi et al. | 348/45 |
| 5,749,830 A | * 5/1998 | Kaneko et al. | 600/160 |
| 5,751,341 A | * 5/1998 | Chaleki et al. | 348/65 |

FOREIGN PATENT DOCUMENTS

| DE | 44 05 102 A1 | 8/1994 |
| JP | 60-88924 | 5/1985 |
| JP | 62-54215 | 3/1987 |
| JP | 63-304221 | 12/1988 |
| JP | 4-93912 | 3/1992 |
| JP | 4-353818 | 12/1992 |

(List continued on next page.)

Primary Examiner—Gims S. Philippe
(74) Attorney, Agent, or Firm—Armstrong Westerman & Hattori, LLP.

(57) ABSTRACT

An armor (111a) of a scope unit (131) and a diaphragm (123) are arranged to be mutually freely turnable. The shape of an outer section (123c) of the diaphragm (123) and the shape of the inside of a scope joint (130a) of a TV camera unit (130) substantially agree with each other, and the outer section (123c) of the diaphragm (123) and the inside of the scope joint (130a) engage with each other. In a state in which the outer section (123c) of the diaphragm (123) and the inside of the scope joint (130a) are engaged with each other, a ring screw (133) is meshed with a thread (130b) so that the scope unit (131) and TV camera unit (130) will unitedly be joined with each other. At this time, since the outer section (123c) of the diaphragm (123) is engaged with the scope joint (130a), the diaphragm and TV camera unit can be turned relative to an objective optical system (119) and relay optical system (121) with the optical axis of the relay optical system (121) as an axis of turning. Moreover, a liquid-crystal shutter 124 in the TV camera unit (130) has two interceptive areas (124a, 124b) which can be switched temporally alternately. The interceptive areas (124a, 124b) intercept one of two light beams passing through either of aperture stops (123a, 123b).

15 Claims, 14 Drawing Sheets

FOREIGN PATENT DOCUMENTS

| | | |
|---|---|---|
| JP | 5-341207 | 12/1993 |
| JP | 6-59199 | 3/1994 |
| JP | 6-160731 | 6/1994 |
| JP | 6-167658 | 6/1994 |
| JP | 6-194580 | 7/1994 |
| JP | 6-202006 | 7/1994 |
| JP | 6-254046 | 9/1994 |
| JP | 7-261099 | 10/1995 |
| WO | WO 90/14040 | 11/1990 |
| WO | WO 92/19008 | 10/1992 |

* cited by examiner

FIG.14 A  FIG.14 B
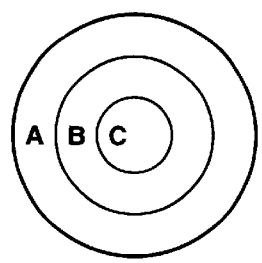
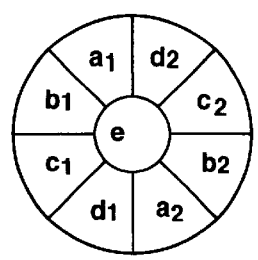
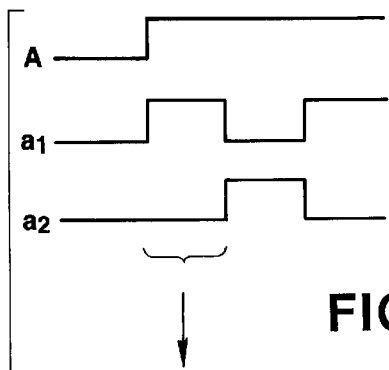
FIG.15A
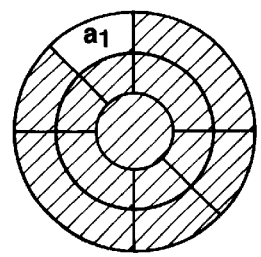
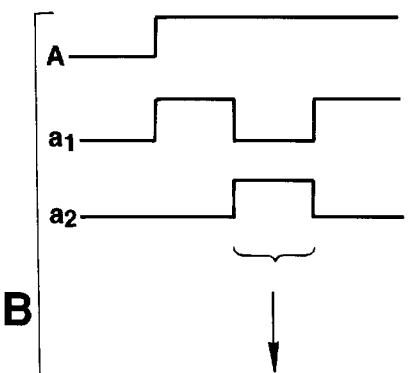
FIG.15B
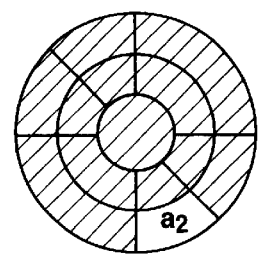

FIG.16A
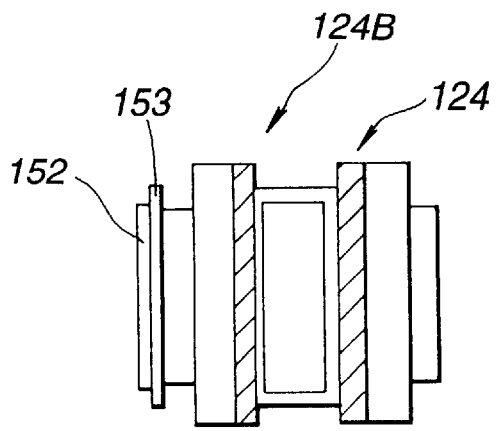
FIG.16B  FIG.16C  FIG.16D
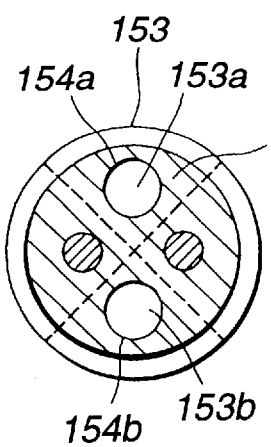 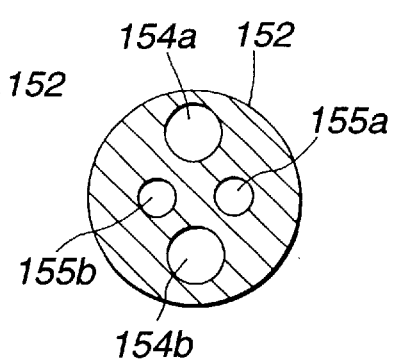 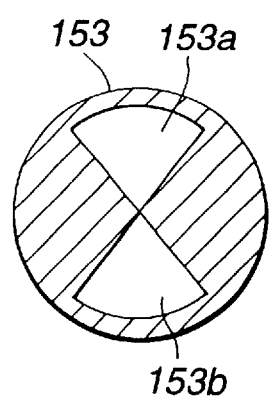
FIG.16E
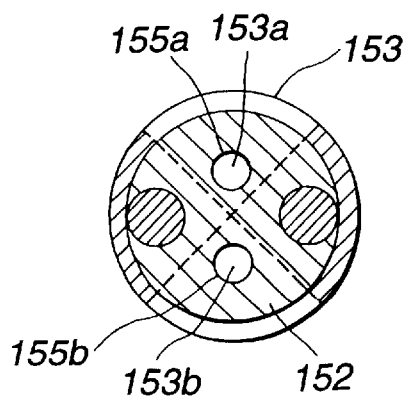

FIG.17A
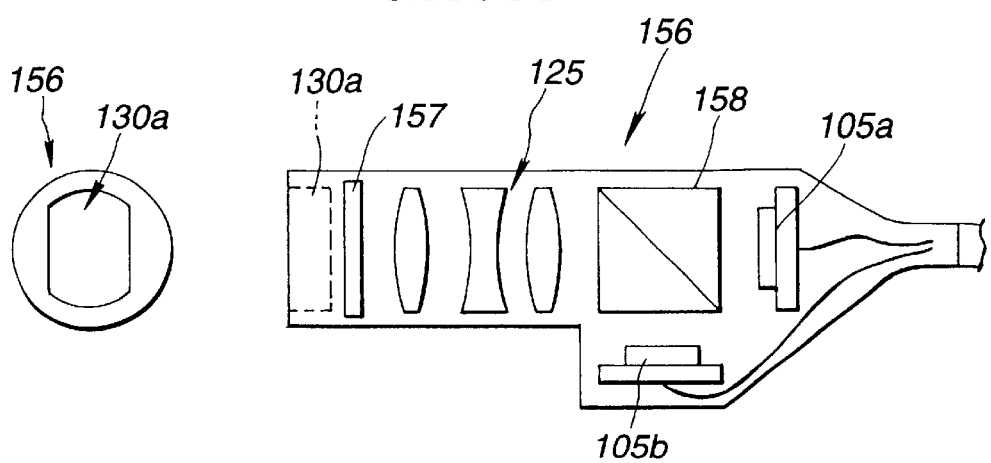
FIG.17B
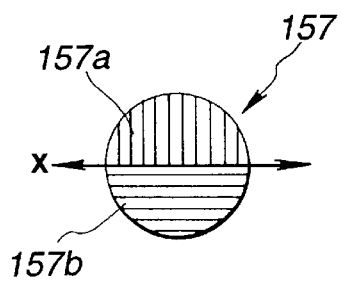
FIG.18A
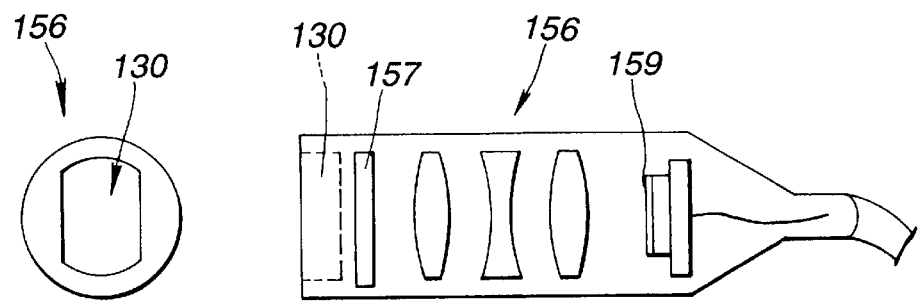
FIG.18B    FIG.18C    FIG.18D
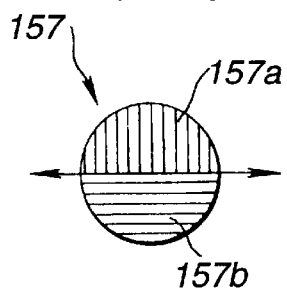 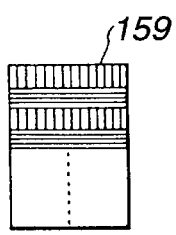 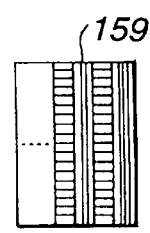

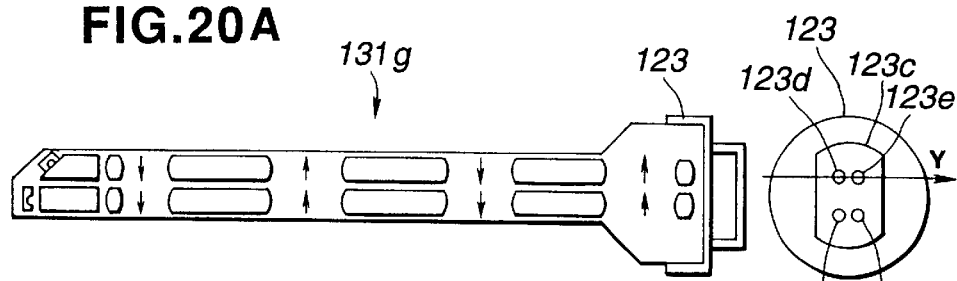
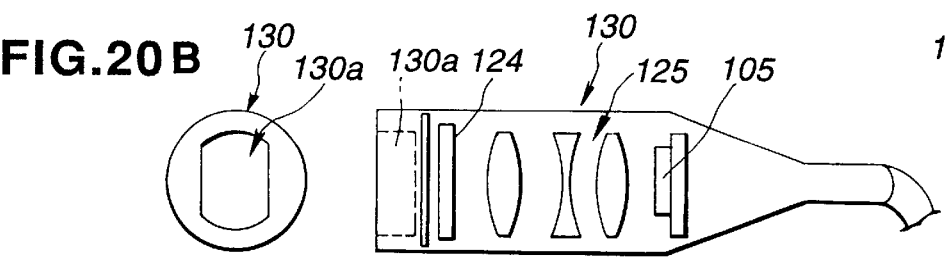
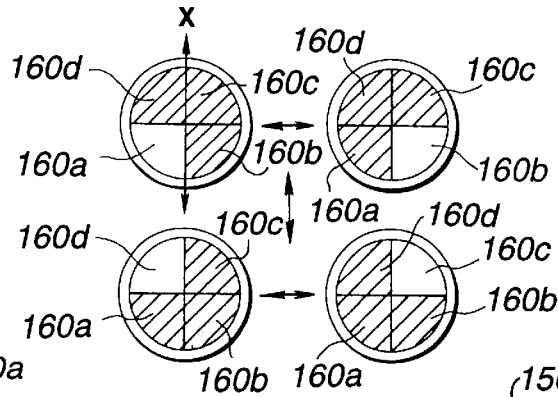
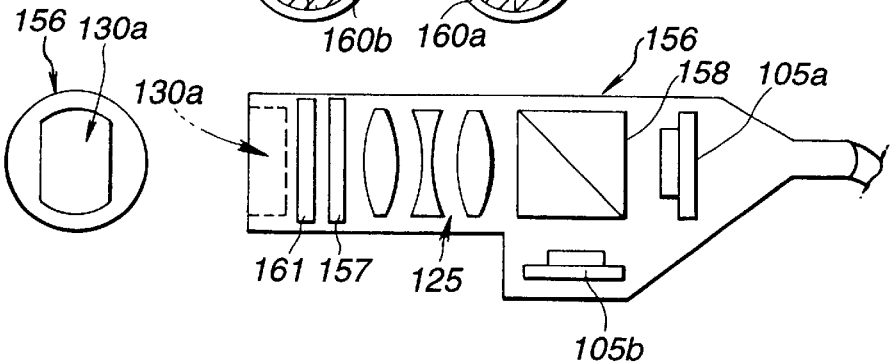
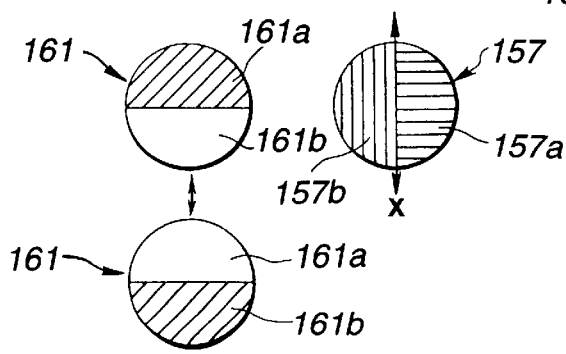

STEREOSCOPIC ENDOCSOPE SYSTEM AND TV IMAGING SYSTEM FOR ENDOSCOPE

TECHNICAL FIELD

The present invention relates to a stereoscopic endoscope system and a TV imaging system for an endoscope which are used to observe an object three-dimensionally.

BACKGROUND TECHNOLOGY

In recent years, endoscopes each having an elongated insertion unit thereof inserted in a body cavity for observation of an organ in the body cavity and making it possible to use if necessary a treatment appliance inserted in a treatment appliance channel to conduct various curative procedures have been adopted widely. Moreover, industrial endoscopes have been widely utilized for observation, inspection, or the like of flaws, corrosion, or the like inside a pipe in a boiler, gas turbine, engine, chemical plant, or the like or inside a body of an automobile engine.

The endoscopes include a flexible endoscope whose insertion unit is flexible and inserted in a curved body cavity through a mouth or the like in order to observe or diagnose a lesion in the body cavity, and a rigid endoscope whose insertion unit is rigid and inserted linearly to an intended region.

In case the flexible endoscope is of an optical type, a flexible image guide fiber is used as an image conveying means. The rigid endoscope has an excellent target-finding ability owing to its rigid insertion unit, wherein a relay optical system is usually used as an image conveying means to produce an optical image.

The endoscopes including the rigid endoscope fall into a type in which an optical image is observed directly by naked eyes and a type in which an optical image picked up by a solid-state imaging device such as a charge-coupled device (CCD) serving as an imaging means is displayed in a monitor screen for observation.

With advancements in surgical procedures, endoscopic surgery, in which a small orifice is created in the abdomen in order to observe the abdominal cavity or conduct an operation thereon using an endoscope, is prevailing as a substitute for conventionally-adopted laparotomy. Almost all the foregoing endoscopes are designed to visualize a body cavity as a planar image that cannot give depth perception.

As far as the known endoscopes for viewing a planar image are concerned, it is hard to observe minute irregularity on the surface of, for example, an inner wall of a body cavity which is a very important diagnostic indication. In an effort to overcome this drawback, a stereoscopic endoscope in which optical systems are arranged in an endoscope, which is designed for producing a planar image for observation, in such a manner that three-dimensional observation is enabled has been proposed.

The optical systems for an endoscope enabling stereoscopy fall into three types described below.

First, a stereoscopic endoscope 10 of, as shown in FIG. 1, a dual-objective dual-relay optical system type has been disclosed in Japanese Patent Laid-Open No. 6-160731. The stereoscopic endoscope 10 is configured by juxtaposing two identical optical systems.

In the stereoscopic endoscope 10, as shown in FIG. 1, images 13a and 13b formed by objective optical systems 12a and 12b incorporated in a scope unit 11 are transmitted by a given distance by conveying optical systems 14a and 14b formed with systems of relay lenses. The images are then recomposed into parallel rays by lenses 15a and 15b and transmitted to a TV camera unit 16.

The images transmitted to the TV camera unit 16 are formed on imaging planes of two imaging devices 18a and 18b by way of image formation lenses 17a and 17b, whereby optical images are produced. Reference numeral d1 denotes a spacing between two optical axes that is comparable to a parallax.

Secondly, as shown in FIG. 2, a stereoscopic endoscope 20 of a single-objective single-relay optical system type is described in Japanese Patent Laid-Open No. 6-167658. In the stereoscopic endoscope 20, a system of relay lenses serving as an objective optical system and conveying optical system is formed with a single optical system that is axially symmetric.

In the stereoscopic endoscope 20, as shown in FIG. 2, a pair of right and left aperture stops 23a and 23b and image formation lenses 24a and 24b are located at a position 22 of image formation at the back end of the system of relay lenses 21 so that the aperture stops will have a spacing corresponding to a parallax d2 between them. An image is therefore spatially split into two portions. Thus, a pair of right and left images having a parallax between them are formed on two imaging devices 25a and 25b, whereby optical images are produced.

Thirdly, the present applicant has disclosed a stereoscopic endoscope 30 of a dual-objective single-relay optical system type as shown in FIG. 3 in Japanese Patent Laid-Open No. 7-261099.

In the stereoscopic endoscope 30, as shown in FIG. 3, a pair of right and left systems of lenses are used as first groups of lenses 32a and 32b of an objective optical system 31 and placed so that aperture stops of the systems will have a spacing d3 between them. A second group 33 of lenses of the objective optical system 31, and systems of relay lenses 34a, 34b, and 34c serving as a conveying optical system are each formed with a single optical system that is axially symmetric. An image passing through entrance pupil formation lenses 35 located at the back end of these systems of relay lenses 34a, 34b, and 34c is spatially split by aperture stops 36a and 36b. Resultant right and left images are formed on two imaging devices 38a and 38b by a pair of right and left image formation lenses 37a and 37b, whereby optical images are produced.

One of the advantages of the stereoscopic endoscope 10 of a dual-objective dual-relay optical system type shown in FIG. 1 is that a three-dimensional image can be produced merely by juxtaposing normal optical systems designed for an endoscope. For optimizing three-dimensionality, the spacing dl between the optical axes of objective optical systems should merely be varied. In this case, the optimization can be achieved irrespective of specifications including an angle of view. The stereoscopic endoscope of this type can be designed more easily than the stereoscopic endoscope 20 of a single-objective single-relay optical system type shown in FIG. 2.

By contrast, one of the drawbacks of the stereoscopic endoscope 10 lies in that since the right and left optical systems are constructed independently, the number of parts is large. Consequently, assembling is complex. Moreover, a difference in magnification between right and left images occurs deriving from an error of each part, and a shift of a focal point are large, and fine adjustment is required for normal stereoscopy.

One of the advantages of the stereoscopic endoscope 20 of a single-objective single-relay optical system type shown in FIG. 2 is that the structures of an objective optical system and system of relay lenses are identical to those of normal optical systems designed for an endoscope. Therefore, while right and left images are sharing the same optical path, a change of an image deriving from errors caused during manufacturing occurs in the right and left images in the same manner. A difference in magnification between the right and left images and a shift of a focal point are therefore small. Moreover, since the number of parts is small, assembling efficiency is good. When as described in Japanese Patent Laid-Open No. 6-59199, a system of relay lenses is integrated into a scope unit and image formation lenses and imaging devices are integrated into a TV camera unit, the orientations of images can be corrected by turning the units relative to each other.

On the other hand, one of the drawbacks of the stereoscopic endoscope 20 is that three-dimensionality cannot be determined irrespective of specifications including an angle of view. The spacing between right and left entrance pupils of aperture stops that determines three-dimensionality is determined by an angle of view of an objective optical system, a numerical aperture of a system of relay lenses, a spacing between the aperture stops, and the like. Normally, the diameter of an aperture stop of an objective optical system is smaller than that of a system of relay lenses. As long as the outer diameter of an insertion unit is identical to that of the stereoscopic endoscope 10 of a dual-objective dual-relay optical system type shown in FIG. 1, three-dimensionality is poorer.

One of the advantages of the stereoscopic endoscope 30 of a dual-objective single-relay optical system type shown in FIG. 3 is that three-dimensionality can be optimized irrespective to specifications including an angle of view by varying the spacing d3 between optical axes of the two first groups of lenses of the objective optical system. Moreover, since right and left images share the same optical path in the range from the second group of lenses of the objective optical system to the entrance pupil formation lenses, a difference in magnification between the right and left images and a shift of a focal point are small. Besides, since the number of parts is small, assembling efficiency is good.

By contrast, a drawback of the stereoscopic endoscope 30 lies in that when lenses ending with the entrance pupil formation lenses are integrated into a scope unit and lenses succeeding the entrance pupil formation lenses are integrated into a TV camera unit, the orientations of images cannot be corrected by turning the units relative to each other. This is because the positions of the right and left aperture stops of the scope unit are fixed by the first group of lenses of the objective optical system. Light beams are therefore obstructed by the turning.

As mentioned above, the three typical types of stereoscopic endoscopes have both advantages and disadvantages. The endoscopes have therefore been used selectively according to the purpose of use.

However, even in case the stereoscopic endoscopes are used selectively according to the purpose of use, the drawbacks below occur.

In the stereoscopic endoscope 20 and stereoscopic endoscope 30, scope units that are mutually different in terms of a diameter of an aperture stop or a spacing between aperture stops; that is, in terms of an outer diameter can be switched and coupled with one TV camera unit.

This is because that the positions of the pair of the right and left aperture stops and the spacing between the optical axes of the image formation lenses in the stereoscopic endoscope 20 shown in FIG. 2 are fixed. Therefore, if a scope unit whose relay optical system has an aperture stop of a small diameter is mounted, light beams are obstructed. On the contrary, if a scope whose relay optical system has an aperture stop of a large diameter is mounted, light rays that cannot be extracted increase in number. This leads to a larger amount of wasted light. When a plurality of scope units having different diameters are prepared and used selectively according to the purpose of use, it becomes necessary to prepare a plurality of TV camera units in line with the scope units. This poses a serious problem costwise.

Moreover, even if any type of TV camera unit is used, it is impossible to replace the corresponding scope unit with any other type of scope unit and couple it with the TV camera unit. Since the TV camera units are mutually incompatible, when a plurality of scope units are prepared to cope with different purposes of use, it is required to prepare a plurality of TV cameras. This poses a problem costwise.

Moreover, whichever type of TV camera unit is used, the TV camera unit is dedicated to a stereoscopic endoscope. The TV camera unit is incompatible with the one for a rigid scope used for normal observation.

In any type of TV camera unit, the TV camera unit has a pair of right and left image formation lenses. This leads to a large number of parts. Moreover, since there is a difference between right and left images, focusing or the like is needed.

DISCLOSURE OF THE INVENTION

A stereoscopic endoscope system in accordance with the first invention comprises: a scope unit including at least one objective optical system located in an elongated insertion unit, and at least one conveying optical system for conveying an object image formed by the objective optical system; and a TV camera unit including one image formation optical system for imaging a light beam emanating from the scope unit, and an imaging device for picking up images passing through the image formation optical system. The stereoscopic endoscope system is characterized in that the scope unit and TV camera unit are detachable from each other, and that an image disuniting member for disuniting a plurality of images is incorporated in the TV camera unit.

According to the first invention, the image disuniting member incorporated in the TV camera unit detachable from the scope unit can disunite a plurality of images.

A TV imaging system for an endoscope in accordance with the second invention comprises a scope unit having an elongated insertion unit that can be inserted in a narrow region and a TV camera unit that can be attached to the scope unit. The TV imaging system is characterized in that the TV camera unit includes a single image formation optical system, a stop splitting member for temporally splitting an aperture stop of the image formation optical system, and an imaging device for photoelectrically transferring images formed by the image formation optical system, and that the member for temporally splitting the aperture stop temporally switches a state, in which one of two areas constituting the aperture stop of the image formation optical system is transparent and the other area is interceptive, and a state in which the one of the two areas is interceptive and the other area is transparent.

According to the second invention, the aperture stop of the image formation optical system can be split temporally by temporally switching the state, in which one of two areas constituting the aperture stop of the image formation optical system is transparent and the other area is interceptive, and the state in which the one of the two areas is interceptive and the other area is transparent.

BRIEF DESCRIPTION OF THE DRAWINGS

FIG. 1 is an explanatory diagram showing the configuration of a dual-objective dual-relay optical system type scope unit;

FIG. 2 is an explanatory diagram showing the configuration of a single-objective single-relay optical system type scope unit;

FIG. 3 is an explanatory diagram showing the configuration of a dual-objective single-relay optical system type scope unit;

FIGS. 4 to 6 show an embodiment of the present invention;

FIG. 4 is an explanatory diagram showing the overall configuration of a stereoscopic endoscope system;

FIG. 5 are explanatory diagrams showing the configurations of scope units of different types;

FIG. 6 is an explanatory diagram showing a scope unit and TV camera unit in a stereoscopic endoscope system;

FIG. 7 are diagrams showing an automatic focusing mechanism in a TV camera unit in a stereoscopic endoscope system;

FIG. 8 are diagrams showing the outline structure of a liquid-crystal shutter;

FIG. 9 are diagrams for explaining an optical system located in the vicinity of a junction between a scope unit and TV camera unit shown in FIG. 5A or 5B;

FIG. 10A is an explanatory diagram showing the outline configuration of the shutter made using a mechanical interceptive plate;

FIG. 10B is a diagram showing the structure of the interceptive plate;

FIG. 12A is an explanatory diagram showing the scope unit;

FIG. 12B is an explanatory diagram showing the TV camera unit;

FIG. 14 are diagrams for explaining examples of an electrode pattern of transparent electrodes arranged in a liquid-crystal shutter;

FIG. 14A is a diagram showing one electrode pattern of transparent electrodes;

FIG. 14B is a diagram showing another electrode pattern of transparent electrodes;

FIG. 15 are diagrams for explaining examples of the state of a liquid-crystal shutter attained with application of a voltage;

FIG. 15A is a diagram showing a state in which a voltage is applied to transparent electrodes in order to bring area a1 alone of the liquid-crystal shutter to a transparent state;

FIG. 15B is a diagram showing a state in which a voltage is applied to the transparent electrodes in order to bring area a2 alone of the liquid-crystal shutter to a transparent state;

FIG. 16 are diagrams for explaining another structure of a liquid-crystal shutter;

FIG. 16A is an explanatory diagram showing the structure of the liquid-crystal shutter which is provided with the capability of a diaphragm by means of a first aperture plate and second aperture plate;

FIG. 16B is a diagram showing the diaphragm formed with two aperture plates from the front thereof;

FIG. 16C is an explanatory diagram showing the first aperture plate constituting the diaphragm of the liquid-crystal shutter;

FIG. 16D is an explanatory diagram showing the second aperture stop constituting the diaphragm of the liquid-crystal shutter;

FIG. 16E is a diagram showing a state in which the relative position of one aperture plate is changed;

FIG. 17 are diagrams for explaining another configuration of a TV camera unit;

FIG. 17A is an explanatory diagram showing the configuration of a TV camera unit in which polarizing plates permitting mutually perpendicular polarizing directions;

FIG. 17B is a diagram showing the structure of a polarizing plate;

FIG. 18 are diagrams showing another configuration of a TV camera unit;

FIG. 18A is an explanatory diagram showing the configuration of a TV camera unit in which a slit type polarizing plate is placed on the front side of an imaging device on behalf of a deflection beam splitter;

FIG. 18B is a diagram showing the structure of a polarizing plate;

FIG. 18C is a diagram showing an example of the structure of a slit type polarizing plate;

FIG. 18D is a diagram showing another example of the structure of the slit type polarizing plate;

FIGS. 19 and 20 are diagrams for explaining a rigid scope in which one scope unit includes two observation optical systems permitting different field-of-view directions;

FIG. 19 are diagrams for explaining a scope unit in which optical systems are juxtaposed;

FIG. 19A is an explanatory diagram showing the configuration of a scope unit;

FIG. 19B is an explanatory diagram showing a TV camera unit to be connected to the scope unit shown in FIG. 19A;

FIG. 19C is a diagram showing split areas of an aperture stop in the TV camera unit shown in FIG. 19B;

FIG. 20 are diagrams for explaining a scope unit in which two sets of a single objective optical system and single relay optical system are juxtaposed;

FIG. 20A is an explanatory diagram showing the configuration of the scope unit;

FIG. 20B is an explanatory diagram showing a TV camera unit to be connected to the scope unit shown in FIG. 20A;

FIG. 20C includes diagrams showing split areas of an aperture stop in the TV camera unit shown in FIG. 20B;

FIG. 20D is an explanatory diagram showing the configuration of a TV camera unit including a polarizing plate; and FIG. 20E is a diagram showing split areas of the polarizing plate.

BEST MODES FOR CARRYING OUT THE INVENTION

Figure 1:
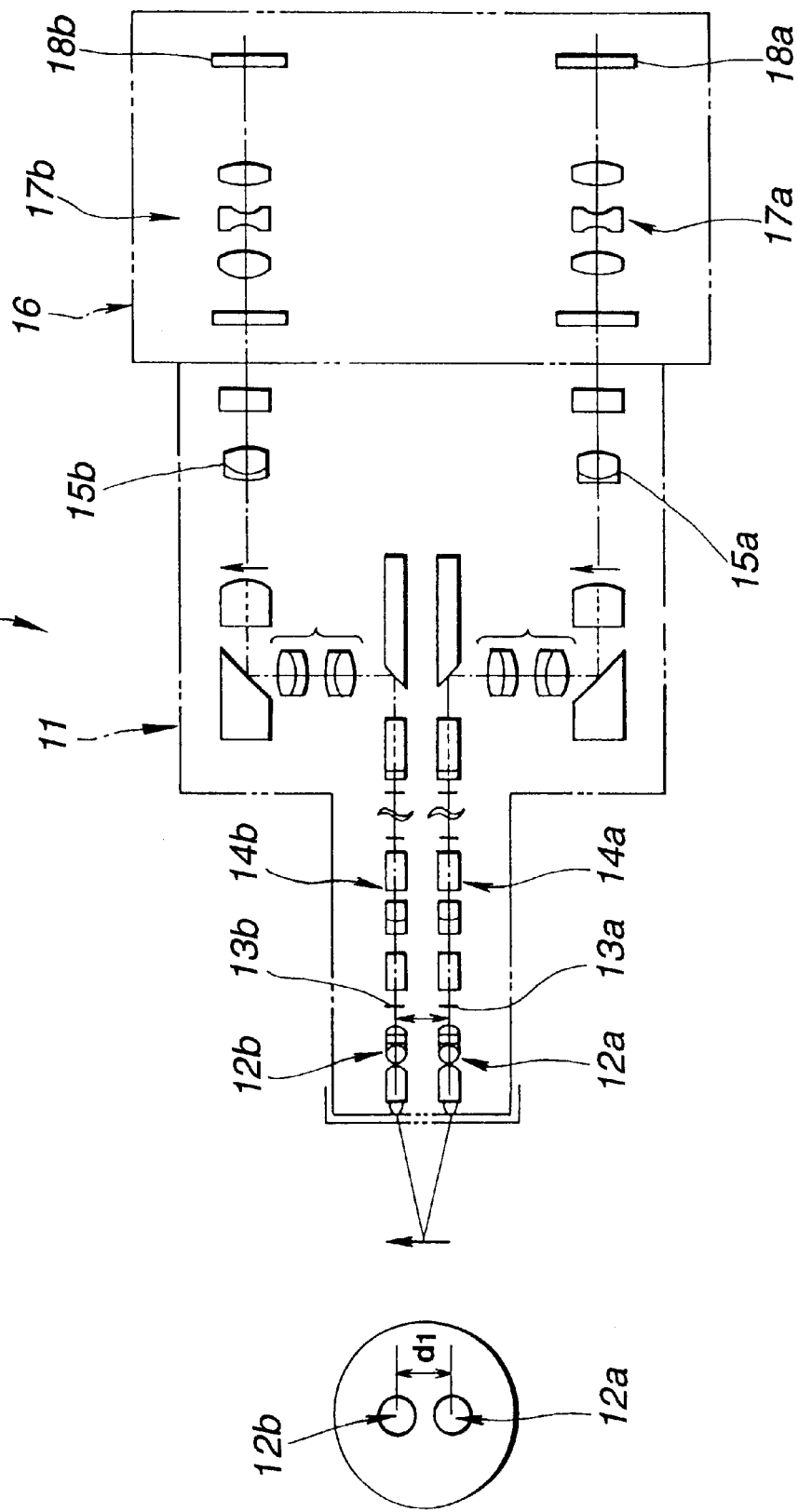
FIGS. 1 to 3 are explanatory diagrams showing the outline configurations of known scope units.
Figure 2:
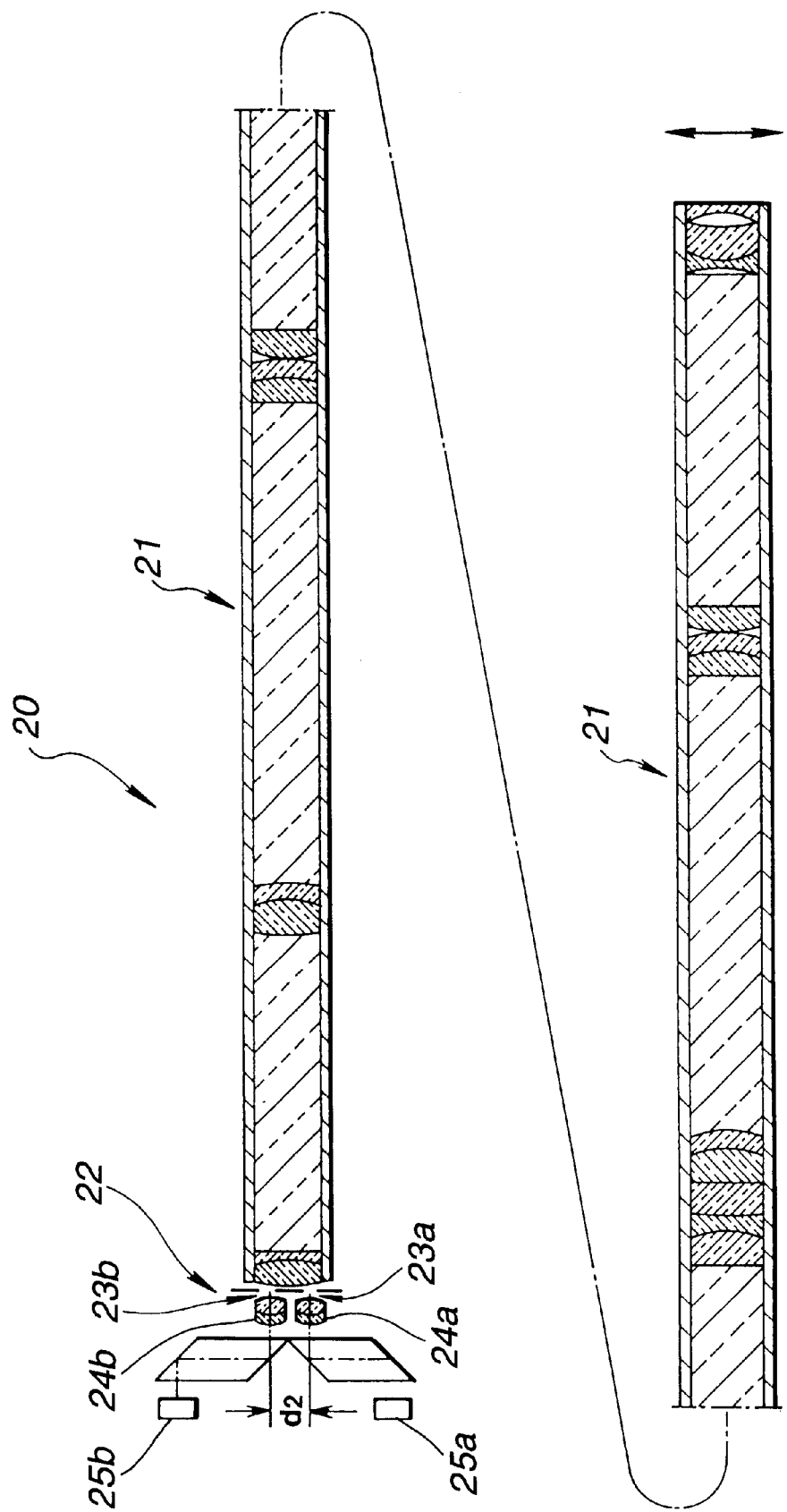
Figure 3:
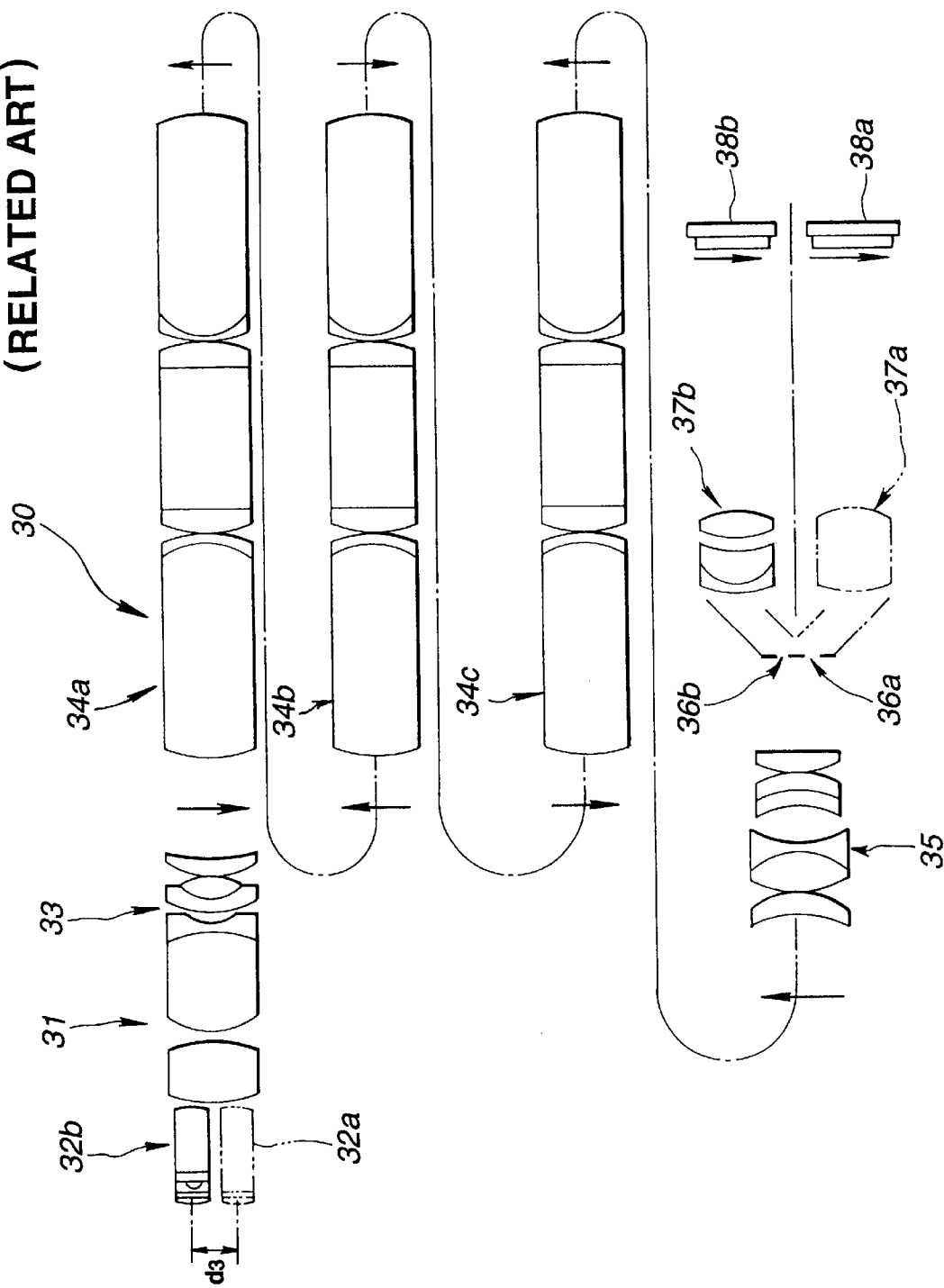

Referring to the drawings, embodiments of the present invention will be described below.

Figure 4:
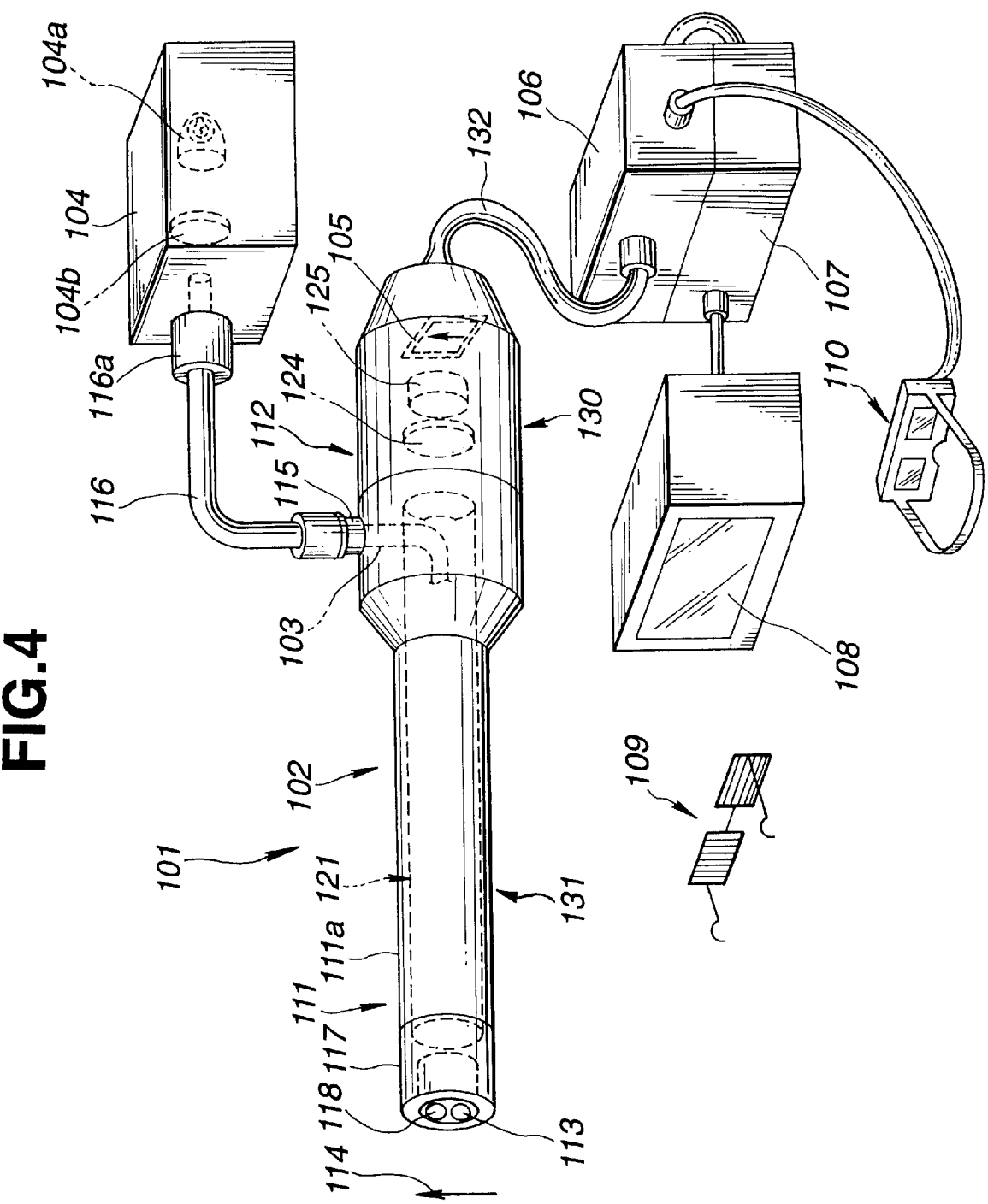
Figure 5A:
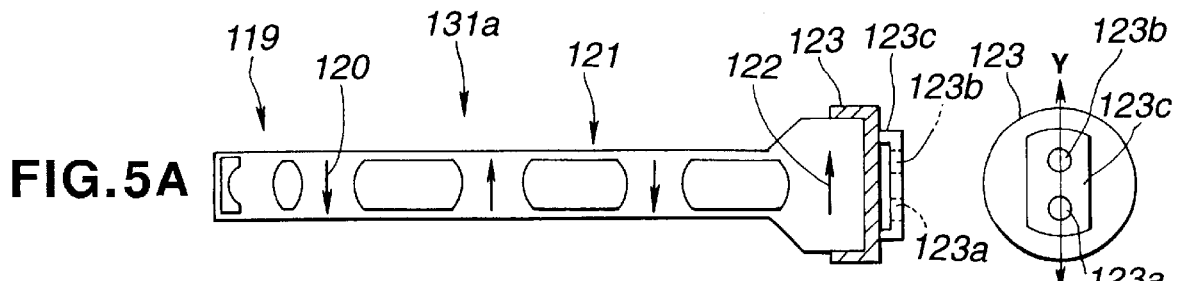
FIG. 5A is an explanatory diagram showing the configuration of a single-objective single-relay optical system type scope unit.
Figure 5B:
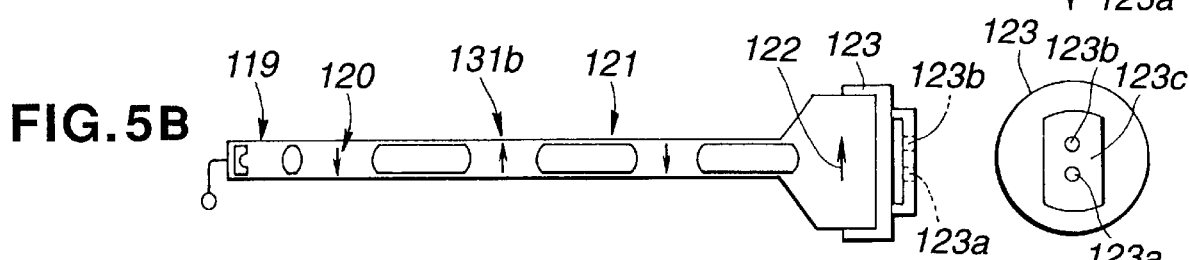
FIG. 5B is an explanatory diagram showing the configuration of a single-objective single-relay optical system type scope unit of which insertion unit has a smaller diameter than that of the scope unit shown in FIG. 5A.
Figure 5C:
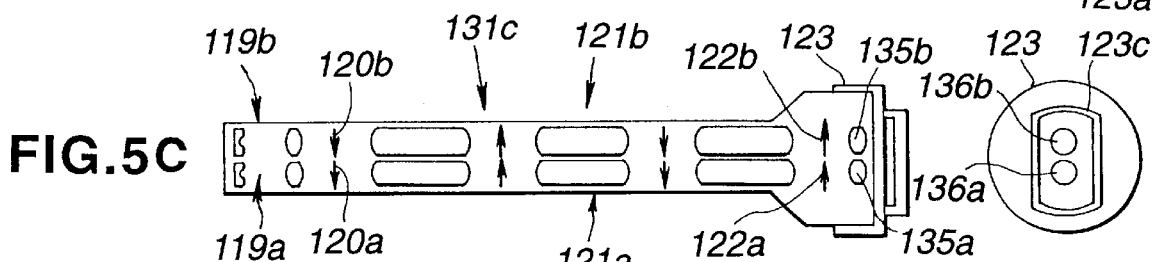
FIG. 5C is an explanatory diagram showing the configuration of a dual-objective dual-relay optical system type scope unit.
Figure 5D:
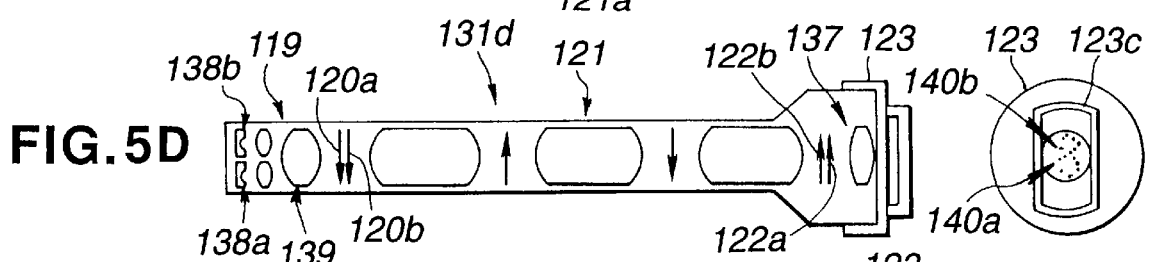
FIG. 5D is an explanatory diagram showing the configuration of a dual-objective dual-relay optical system type scope unit.
Figure 5E:
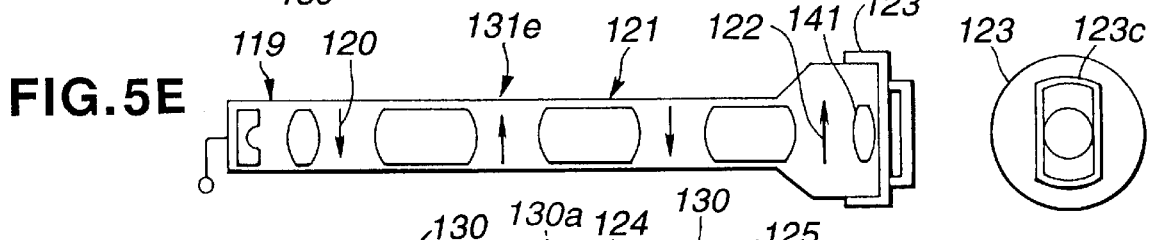
FIG. 5E is an explanatory diagram showing the configuration of a rigid scope used for normal observation.
Figure 5F:
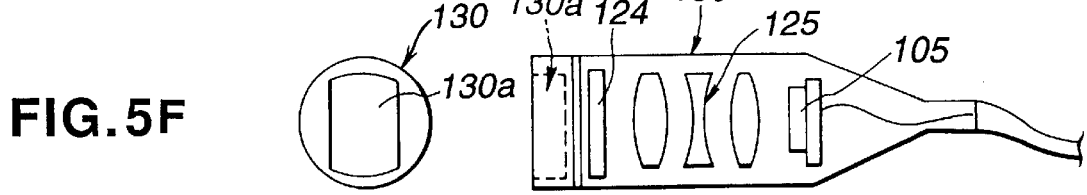
FIG. 5F is an explanatory diagram showing the configuration of a TV camera unit that can be connected to the scopes shown in FIGS. 5A, 5B, 5C, 5D, and 5E.
Figure 5G:
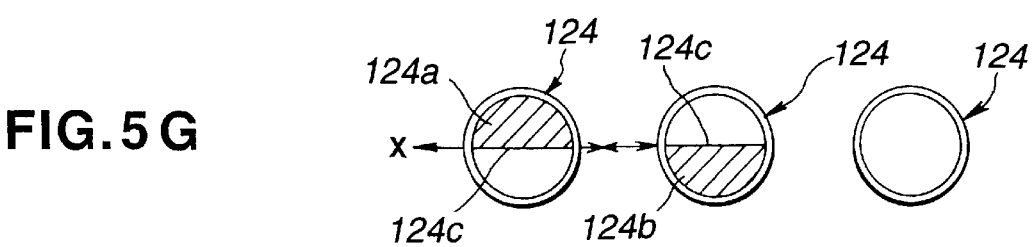
FIG. 5G is an explanatory diagram showing a liquid-crystal shutter in a TV camera unit.
Figure 6:
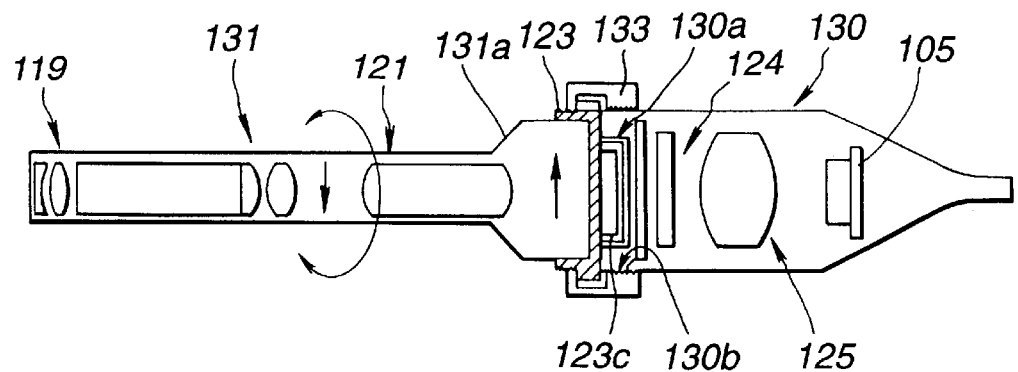

Referring to FIGS. 4 to 6, the first embodiment of the present invention will be described.

As shown in FIG. 4, a stereoscopic endoscope system 101 comprises: a stereoscopic endoscope 102 including an imaging optical system and illumination optical system used for stereoscopy; a light guide 103 serving as an illumination light conveying means lying through the stereoscopic endoscope 102; a light source apparatus 104 including, for example, a lamp 104a for generating illumination light of white light and thus supplying the illumination light, and a lens 104b for converging the white light; a camera control unit 106 (hereinafter a CCU 106) for processing electric signals sent from an imaging device 105 serving as an imaging means incorporated in the stereoscopic endoscope 102; a scan converter 107 for converting signals output from the CCU 106 into video signals; a color monitor 108 for displaying video signals output from the scan converter 107; shutter glasses 109 having the capability of a shutter for three-dimensionally discerning images displayed on the color monitor 108; and a face-mounted display 110 (hereinafter an FMD 110) to be worn by an operator in order to three-dimensionally discern signals output from the CCU 106.

The stereoscopic endoscope 102 includes an elongated insertion unit 111 to be inserted in a body cavity, and a grip unit 112 located at the back end of the insertion unit 111 and to be gripped by an operator. The insertion unit 111 is formed with an armor 111a that is shaped like a round pipe and that is realized with a rigid metallic member made of stainless steel or the like. In short, the stereoscopic endoscope 102 is a so-called rigid scope having the rigid insertion unit 111.

The insertion unit 111 includes, similarly to that of an electronic endoscope intended to produce a planar image for normal observation, a light guide 103 for conveying illumination light supplied from the light source apparatus 104, and an illumination optical system for irradiating illumination light conveyed by the light guide 103 through an illumination window 113 so as to illuminate an object 114. Moreover, an observation optical system, which will be described later, for producing two views having a parallax between them is included so that the object 114 illuminated by the illumination optical system can be visualized stereoscopically. In this specification, an optical system having the operation of forming two images, which have a parallax between them, on an imaging device having a photoelectric transfer function is used as the observation optical system. The observation optical system is therefore also referred to as an imaging optical system.

The grip unit 112 has a light guide base 115 to which the back end of the light guide 103 is jointed. One end of a light guide cable 116 is connected to the light guide base 115 so that the light guide cable 116 can be detached freely. A light guide connector 116a is attached to the other end of the light guide cable 116, whereby the light guide cable 116 is connected freely detachably to the light source apparatus 104. When the light source apparatus 104 and light guide base 115 are linked by the light guide cable 116, the white light emanating from the lamp 104a is converged by the lens 104b, and irradiated to the end side of the light guide connector 116a. The white light irradiated to the end side is supplied to the light guide 103 by way of the light guide cable 116 and light guide base 115. The light guide 103 is angled inside the grip unit 112 and passed through the insertion unit. The illumination light supplied to the light guide 103 is irradiated through the illumination window 113 formed in a distal section 117 of the insertion unit 111.

Now, an observation optical system will be described with reference to FIG. 5A.

An optical image 120 of the object 114 illuminated by illumination light is formed at a position of image formation by an objective optical system 119 constituting a single-objective single-relay optical system type observation optical system opposed to an observation window 118 adjoining the illumination window 113 of the distal section 117 as shown in FIGS. 4 and 5A. The optical image 120 is conveyed to the back end of the insertion unit 111 by a relay optical system 121. A light beam representing a last image 122 transmitted by the relay optical system 121 is halved by a diaphragm 123 having aperture stops 123a and 123b that are formed mutually separately.

The halved light beams are alternately intercepted by a a means for temporally disuniting a plurality of images, for example, a liquid-crystal shutter 124, and finally formed on an image formation plane of the imaging device 105, which is a photoelectric transfer plane, through image formation lenses 125. As shown in FIG. 4, the shape of the imaging plane of the imaging device 105 is, for example, a square. The imaging device 105 is placed so that lengthwise or sideways direction of the imaging plane of the imaging device 105 will coincide with the lateral direction of the two aperture stops 123a and 123b which are formed mutually separately.

The grip unit 112 constitutes a TV camera unit 130 in which the liquid-crystal shutter 124 for temporally disuniting images, image formation lenses 125, and imaging device 105 are incorporated. The insertion unit 111 constitutes a scope unit 131 including the light guide 103, illumination window 113, observation window 118, objective optical system 119, and relay optical system 121.

As shown in FIGS. 5F and 6, the armor 111a of the scope unit 131 and the diaphragm 123 are designed to be freely turnable. The shape of an outer section 123c of the diaphragm 123 and the shape of the inside of a scope joint 130a of the TV camera unit 130 substantially agree with each other, and the outer section 123c and the inside of the scope joint 130a engage with each other. In a state in which the outer section 123c of the diaphragm 123 and the inside of the scope joint 130a of the TV camera unit 130 are engaged with each other, a ring screw 133 mounted on the scope unit 131 is meshed with a thread 130b formed on the TV camera unit 130. Thus, the diaphragm 123 and TV camera unit 130; that is, the scope unit 131 and TV camera unit 130 are unitedly joined with each other.

At this time, since the outer section 123c of the diaphragm 123 is engaged with the scope joint 130a of the TV camera unit 130, the diaphragm and TV camera unit can be turned relative to the objective optical system 119 and relay optical system 121 with the optical axis of the relay optical system 121 as an axis of turning.

As shown in FIG. 5G, the liquid-crystal shutter 124 in the TV camera unit 130 has two interceptive areas 124a and 124b which are switched temporally alternately. The interceptive areas 124a and 124b are defined to intercept one of two light beams passing through either of the aperture stops 123a and 123b.

The imaging device 105 and CCU 106 are linked by a signal cable 132 extending from the back end of the TV camera unit 130. Electric signals produced by photoelectrically transferring images that are temporally disunited while passing through the two aperture stops 123a and 123b and that are then formed on the imaging device 105 are processed into image signals by the CCU 106. The image signals are output to the scan converter 107, converted into video signals, and then output to the color monitor 108. At this time, images passing through the two aperture stops 123a and 123b and having a parallax between them are displayed on the color monitor 108 on a time-sharing basis. The images displayed on the color monitor 108 are observed by an operator via the shutter glasses 109 or observed through the FMD 110 worn by the operator. Thus, the object 114 can be discerned three-dimensionally.

Now, the scope unit 131 will be described with reference to FIG. 5.

FIG. 5A shows a single-objective single-relay optical system type scope unit 131a. In the scope unit 131a, an objective optical system 119, relay optical system 121, and diaphragm 123 are arranged in that order from the object side. An optical image 120 formed by the objective optical system 119 is conveyed to the proximal side by the relay optical system 121. A light beam representing a last image 122 conveyed by the relay optical system 121 is split by a diaphragm 123, and emitted from the scope unit 131a to a TV camera unit 130 engaged with and connected to an outer section 123c of the diaphragm 123. The diaphragm 123 has two aperture stops 123a and 123b, and is placed to be axially symmetric with respect to the optical axis of the relay optical system 121. Three-dimensionality, brightness, or the like can be optimized by adjusting the spacing between the two aperture stops 123a and 123b and the diameter of each of them. A direction Y in which the aperture stops 123a and 123b are separated from each other, and a direction X of a border between two interceptive areas 124a and 125b of a liquid-crystal shutter 124 are substantially orthogonal to each other. Images of the aperture stops formed in the image space are so-called exit pupils.

By contrast, FIG. 5B shows a single-objective single-relay optical system type scope unit 131b that resembles the one shown in FIG. 5A but that has a smaller outer diameter than the one shown in FIG. 5A. The spacing between two aperture stops 123a and 123b of the scope unit 131b is narrower than the one shown in FIG. 5A. However, the outer section 123c of the diaphragm 123 of the scope unit 131b has the same shape as the one in FIG. 5A. The TV camera unit 130 can therefore be connected to the scope unit 131b. At this time, a direction Y in which the two aperture stops 123a and 123b are separated from each other, and a direction X of a border between the two interceptive areas of the liquid-crystal shutter 124 are substantially perpendicular to each other. Besides, the two aperture stops 123a and 123b are arranged to be axially symmetric with respect to a border 124c. Even if the spacing between the two aperture stops 123a and 123b is varied, since a field of view will not be obstructed, imaging can be achieved. Aside from the outer diameter, the components are identical to those shown in FIG. 5A.

By contrast, FIG. 5C shows a dual-object dual-relay optical system type scope unit 131c in which two optical system each having the same components as the one shown in FIG. 5B are arranged in parallel. Optical images 120a and 120b formed by objective optical systems 119a and 119b are conveyed to the proximal side as last images 122a and 122b by relay optical systems 121a and 121b, recomposed into substantially parallel rays by lenses 135a and 135b, and then emitted from the scope unit 131c to the TV camera unit 130 engaged with and connected to the outer section 123c of the diaphragm 123.

At this time, when the scope unit 131c and TV camera unit 130 are turned, since the scope unit 131c is of a dual-objective dual-relay optical system type, aperture stops 136a and 136b located at the output end of the scope unit and the liquid-crystal shutter 124 in the TV camera unit 130 are turned relative to each other. In this state, light beams passing through the two aperture stops 136a and 136b cannot be intercepted alternately. The scope unit 131c and TV camera unit 130 may therefore be screwed to and fixed to each other so that they cannot be turned relative to each other. For enabling both the units to make a relative turn, the interceptive areas 124a and 124b of the liquid-crystal shutter 124 is made mechanically or electrically turnable together with the scope unit 131c.

The aperture stops 136a and 136b of the scope unit 131c are defined by right and left lenses 135a and 135b. The diaphragm 123 may not have aperture stops but may have a mere opening.

FIG. 5D shows a dual-objective single-relay optical system type scope unit 131d. The objective optical system 119 having two separate objective-side aperture stops, the relay optical system 121, and an entrance pupil formation lens 137 are arranged in that order from the object side. The objective optical system 119 comprises first optical systems 138a and 138b that are juxtaposed with the optical axes thereof separated from each other and that have the same configuration, and a second optical system 139 placed in order to integrate the optical axes into one optical axis. Two optical images 120a and 120b having a parallax between them are formed at positions that are spatially substantially coincident with each other. The optical images 120a and 120b are relayed to the proximal side by the relay optical system 121 with the sizes thereof unchanged. The optical images are then recomposed into substantially parallel rays by the entrance pupil formation lens 137, and then emitted from the scope unit 131d to the TV camera unit 130 engaged with and connected to the outer section 123c of the diaphragm 123.

At this time, similarly to FIG. 5C, if the scope unit 131d and TV camera unit 130 are turned relative to each other, aperture stops 140a and 140b of the scope unit 131d and the liquid-crystal shutter 124 in the TV camera unit 130 are turned relative to each other. Light beams passing through the two aperture stops 140a and 140b cannot therefore be intercepted alternately. The scope unit 131d and TV camera unit 130 may therefore be screwed to and fixed to each other so that both the units cannot be turned relative to each other. For enabling both the units to make a relative turn, the interceptive areas 124a and 124b of the liquid-crystal shutter 124 are made mechanically or electrically turnable together with the scope unit 131d. The aperture stops 140a and 140b are defined by the first optical systems 138a and 138b located at the distal end. The diaphragm 123 may therefore not have aperture stops but may have a mere opening.

FIG. 5E shows a scope unit 131e for a rigid scope used for normal observation through a planar image. An optical image 120 formed by the objective optical system 119 is conveyed to the proximal side by the relay optical system 121, recomposed into substantially parallel rays by a lens 141, and then emitted from the scope unit 131e to the TV camera unit 130 engaged with and connected to the outer section 123c of the diaphragm 123.

When the TV camera unit 130 is connected to the scope unit 131e for a rigid scope, the liquid-crystal shutter 124 is not actuated but the interceptive areas 124a and 124b are opened. Alternatively, when the liquid-crystal shutter 124 must be actuated, either of right and left images is displayed and thus a normal view is produced. In this rigid scope, the scope unit 131e and TV camera unit 130 can be turned relative to each other with respect to the optical axis of the relay optical system 121.

Moreover, even when the scope unit 131e for a rigid scope is used, if it is connected to the TV camera unit 130, the scope unit can enable stereoscopic observation similarly to any other scope unit. In other words, two portions of a single light beam emitted substantially in parallel from the lens 141 that is an eyepiece lens for an ordinary rigid scope are intercepted alternately by a means for temporally splitting an aperture stop, for example, a liquid-crystal shutter or a mechanical rotary interceptive plate, which is located in the TV camera unit 130. This results in right and left images having a parallax between them.

Specifically, since the outer sections 123c of the diaphragms 123 serving as engaging sections enabling engagement with the TV camera unit 130 in the scope units 131a, 131b, 131c, 131d, and 131e share the same shape, the one TV camera unit 130 can be coupled with any of the scope units 131a, 131b, 131c, 131d, and 131e.

As mentioned above, when outer sections of diaphragms in a plurality of scope units are shaped to engage with the inside of a scope joint in one TV camera unit, the TV camera unit can be made freely attachable to the plurality of scope units. Even if an imaging device that will be used more frequently should break down, it can be repaired or replaced with a new one readily. Moreover, a high-sensitivity TV camera unit or high-resolution TV camera unit having an imaging device with a large number of pixels can be made compatible with scope units that are different from one another in terms of a field-of-view direction, an angle of visibility, three-dimensionality, or an outer diameter. Moreover, when the TV camera unit is made turnable with respect to the optical axis of a relay optical system in the scope unit in a state in which the scope unit and TV camera unit are attached to each other, it becomes possible to correct orientations of images.

Moreover, a TV camera unit uses one image formation optical system to form a plurality of object images, which have a parallax between them, on an imaging means, and the outer sections of diaphragms of a plurality of scope units are shaped to engage with the inside of a scope joint of the one TV camera unit. Consequently, even if a scope unit whose aperture stops have a different diameter or a different spacing between them is attached, observation can be achieved without obstruction of light beams. When the size of an aperture stop in an image formation optical system is set in line with the largest diameter of aperture stops or the largest spacing between them among all diameters or spacings of or between aperture stops of scope units employed, whichever one of the scope units is used, emitted light can be efficiently used for image formation by the image formation optical system without any leakage.

Furthermore, since one image formation optical system is employed in a TV camera unit, an optical system for forming two images having a parallax between them is shared by right and left images. A variation of an image deriving from errors caused during manufacturing therefore occurs in common between the right and left images. There can therefore be provided a TV camera unit characterized by a small error in magnification between the right and left images, a small shift of a focal point, and improved assembling efficiency due to a small number of parts.

Incidentally, the image formation lenses 125 in the TV camera unit 130 may be, for example, a variable-power optical system such as a zoom lens, so that observation can be achieved by enlarging or reducing a picture size in compliance with the different sizes of the last images 122, 122a, and 122b of the scope units. At this time, it is recommended that the variable power should range from about 1.5 to 5 and that the image formation lenses 125 should be made movable in an axial direction in order to enable focusing. Moreover, for a more compact design, an aspherical lens, bending rate distributed type lens, diffraction type lens device, or the like may be used.

Figure 7A:
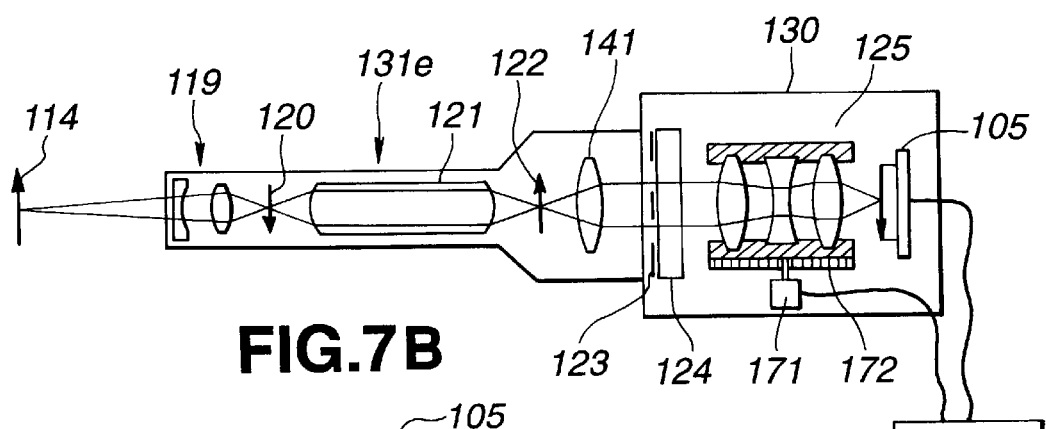
FIG. 7A is an explanatory diagram showing the outline configuration of the automatic focusing mechanism in the TV camera unit.
Figure 7B:
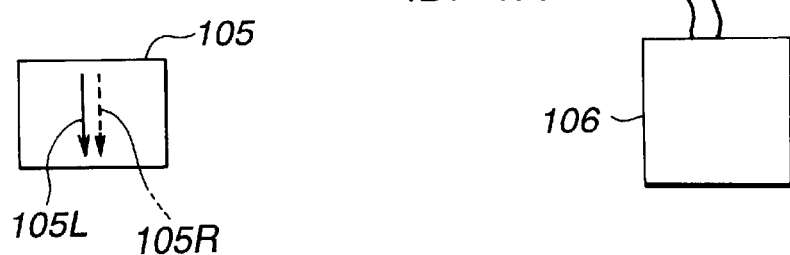
FIG. 7B is a diagram showing a picked-up state of right and left images produced by an imaging device.

Furthermore, focusing a TV camera unit may be automated. In this case, as shown in FIG. 7A, a motor A1 used to move the image formation lenses 125 in an axial direction is incorporated in the TV camera unit. Driving force given by the motor 171 is conveyed to a moving unit 172 formed with a cam or gear in order to move the image formation lenses 125. As shown in FIG. 7B, electric signals representing the produced right and left images 105R and 105L are processed into image signals by the CCU 106. At this time, luminance signals concerning substantially the centers of the right and left images 105R and 105L are used and processed, whereby a mismatch between the centers of the right and left images on the CCD 105 is detected. Based on the mismatch, the CCU 106 outputs a driving signal to the monitor 171 so as to move the image formation lenses 125. Driving the image formation lenses 125 by means of the motor 171 is continued until the mismatch is judged to be zero.

Referring to FIG. 8, the structure of the liquid-crystal shutter 124 will be described.

Figures 8A, 8B:
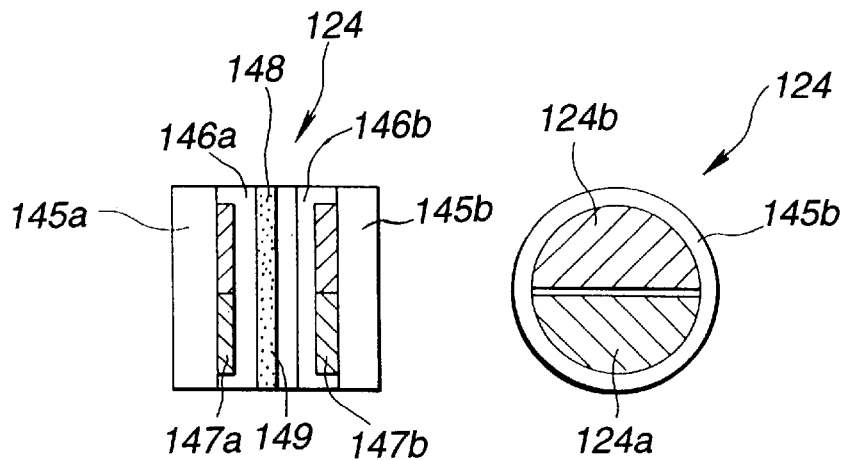
FIG. 8A is an explanatory diagram showing the structure of the liquid-crystal shutter.
FIG. 8B is an explanatory diagram showing two areas of the liquid-crystal shutter.

As shown in FIG. 8A, the liquid-crystal shutter 124 comprises two polarizing plates 145a and 145b, two transparent substrates 146a and 146b, transparent electrodes 147a and 147b formed on the substrates, a liquid-crystal layer 148, and a sealant 149 used to retain the thickness of the liquid-crystal layer 148 at a constant level and lock the liquid crystal at the same time. As for a driving method for the liquid crystal, any of field effect, dynamic scattering, and thermal effect techniques can be employed. A twisted nematic mode (hereinafter a TN mode) based on the field effect technique is most generally adopted and easy to use.

As shown in FIG. 8A, each of the transparent electrode 147a on the substrate 146a and the transparent electrode 147b on the substrate 146b, which are located at both edges, is divided into two areas 124a and 124b. A voltage is applied alternately to the two areas. Thus, as shown in FIG. 8B, the two areas 124a and 124b can be intercepted alternately.

The transmittance attained when the liquid-crystal shutter 124 is intercepted is dependent on an angle of incidence of light. The larger the angle of incidence of light is, the higher the transmittance is. A shutter effect gets weaker. It is therefore recommended that the angle of incidence of light to the liquid-crystal shutter 124 be 20° at maximum, or if possible, at 10° or lower.

Figure 9A:
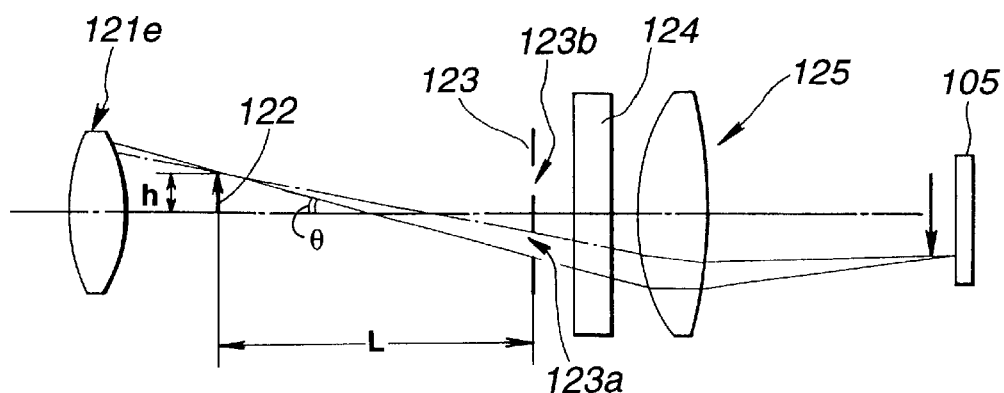
FIG. 9A is an explanatory diagram showing the configuration of the optical system.
Figure 9B:
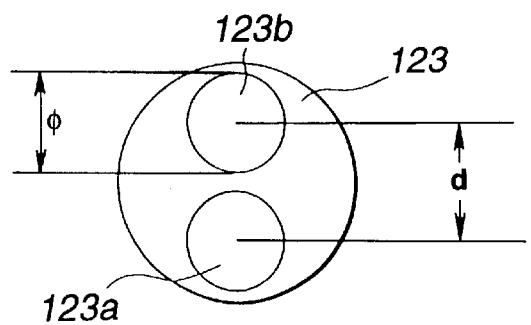
FIG. 9B is an explanatory diagram showing the positional relationship between aperture stops formed in a diaphragm.

Moreover, as shown in FIGS. 9A and 9B, as far as the optical system located in the vicinity of the junction between the scope unit and TV camera unit which is shown in FIG. 5A or 5B is concerned, assuming that the height of the last image 122 produced by a last relay lens 121e is h, the distance of the diaphragm 123 from the last image 122 is L, the diameter of the aperture stops 123a and 123b is ø, and the spacing between the aperture stops 123a and 123b is d, the maximum value θ of an angle of incidence of light to the liquid-crystal shutter 124 is expressed as follows:

$$\theta = \tan^{-1}\{[h+(d+\phi)/2]/L\}$$

Figure 11:
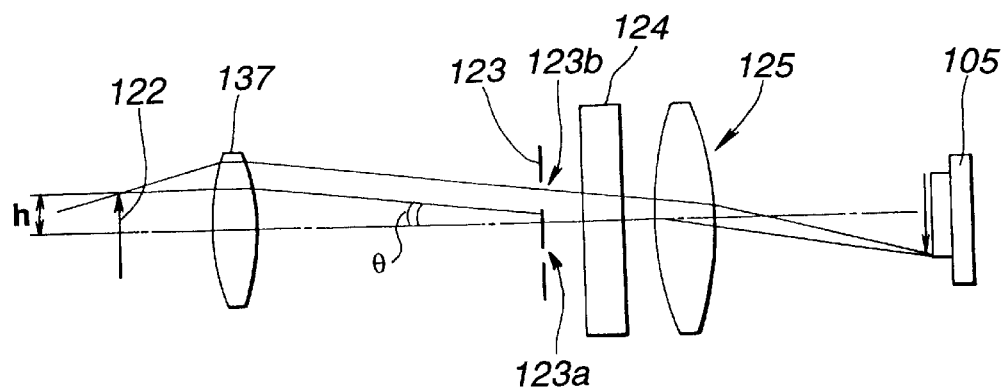
FIG. 11 is an explanatory diagram showing another configuration of an optical system located in the vicinity of the junction between a scope unit and TV camera unit;.

By contrast, in the scope unit shown in FIG. 5D or 5E, as lens 137 is, as shown in FIG. 11, placed behind the last image 122 produced by the last relay lens 121e. Substantially parallel rays are thus emitted from the scope unit 131. In this case, assuming that the height of the last image 122 produced by the last relay lens 121e is h and the focal length of the lens 137 is f, the maximum value θ of the angle of incidence of light to the liquid-crystal shutter 125 is expressed as follows:

$$\theta = \tan^{-1}(h/f)$$

Consequently, the respective parameters should be determined on the assumption that a maximum angle of incident of light to the liquid-crystal shutter 124 is set to 20°, or if possible, 10° or lower.

Figure 10:
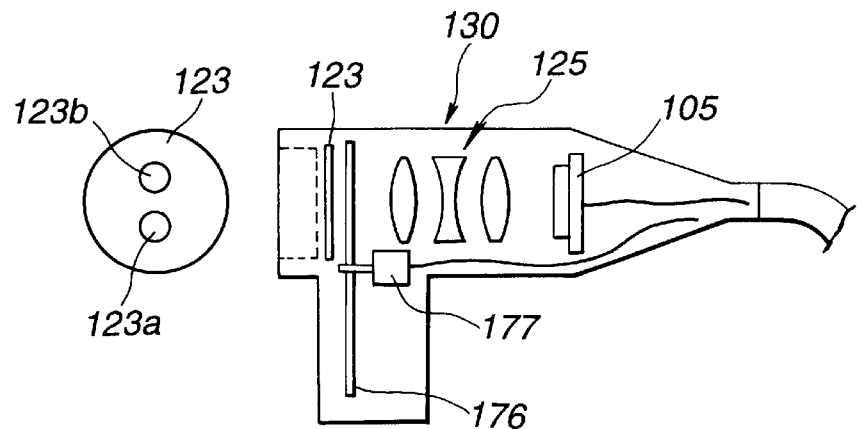
FIG. 10 are diagrams showing a shutter made using a mechanical interceptive plate.
Figure 10:
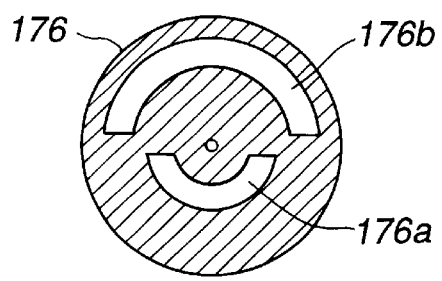

Incidentally, a mechanical interceptive plate may be substituted for the liquid-crystal shutter 124 for temporally disuniting a plurality of images. That is to say, as shown in FIG. 10A, when the mechanical interceptive plate is used to constitute a shutter 175, for example, a round interceptive plate 176 is rotated by means of a motor 177. Since the interceptive plate 176 has, as shown in FIG. 10B, two apertures 176a and 176b, light beams passing through two apertures 123a and 123b formed in a diaphragm 123 shown in FIG. 10A are intercepted alternately. Alternatively, an electro-chromic device utilizing electrochemical reaction, an electrophoretic interceptive device utilizing electro-deposition of colored colloidal particles, or the like will do.

Moreover, an infrared cutoff filter, laser beam cutoff filter, color correction filter, or the like may be incorporated in the TV camera unit 130 if necessary. For a more compact design, it is desired that the filters are united with the liquid-crystal shutter 124 or integrated into one common filter. For example, a method of coating the polarizing plates 145 or transparent substrates 146 constituting the liquid-crystal shutter 124 with a coherent membrane effective for cutting off a laser beam, or a method of using an infrared cutoff filter or color correction filter as the transparent substrates 146 is convenient.

Furthermore, various kinds of solid-state imaging devices generally known by the names of a CCD, PCD, CMD, AMI, SIT, and the like, or image pickup tubes generally known by the names of Saticon, Vidicon, a HARP tube, and the like may be used as the imaging device 105 in the TV camera unit 130. An image intensifier or the like may be used to improve sensitivity.

The imaging device may be of a type in which a single-plate technique is used for color imaging or of a type in which the imaging device is formed as a dual-plate or triple-plate camera for color imaging. Moreover, the imaging device 105 may be incorporated unitedly in the TV camera unit 130, or may be formed as a separate unit so that it can be replaced with a new one.

The stereoscopic endoscope system 101 adopts a simultaneous illumination and imaging method in which the imaging device 105 having a color separation filter such as a mosaic filter is used to achieve color imaging under the illumination of white light. The present invention is not limited to this method, but may apply to a field sequential imaging method in which the imaging device 105 not having a color separation filter is used to produce color component images of three elementary colors under the field-sequential illumination of different kinds of illumination light that have wavelengths of red, green, and blue and that are emitted sequentially to an object.

The liquid-crystal shutter is not limited to the aforesaid structure but may be structured as described below.

Figure 12:
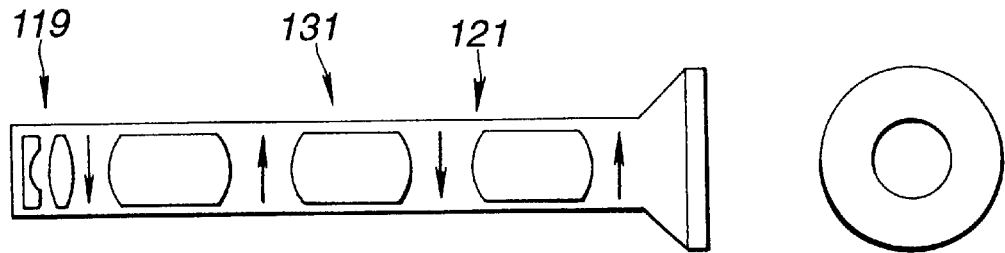
FIG. 12 are diagrams for explaining the scope unit that is shown in FIG. 5A or 5B and devoid of a diaphragm, and a TV camera unit.
Figure 12:
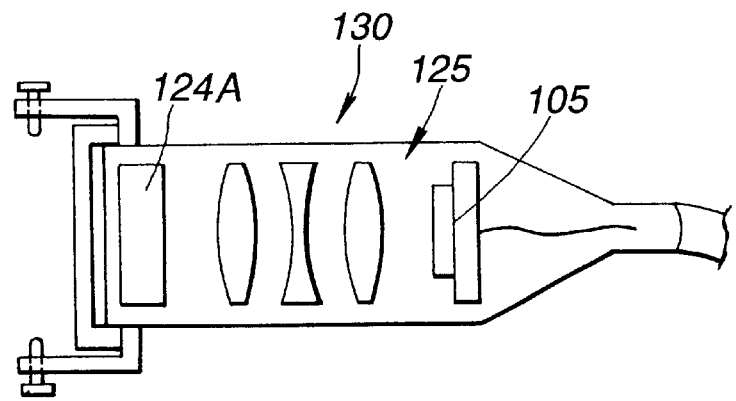
Figure 13:
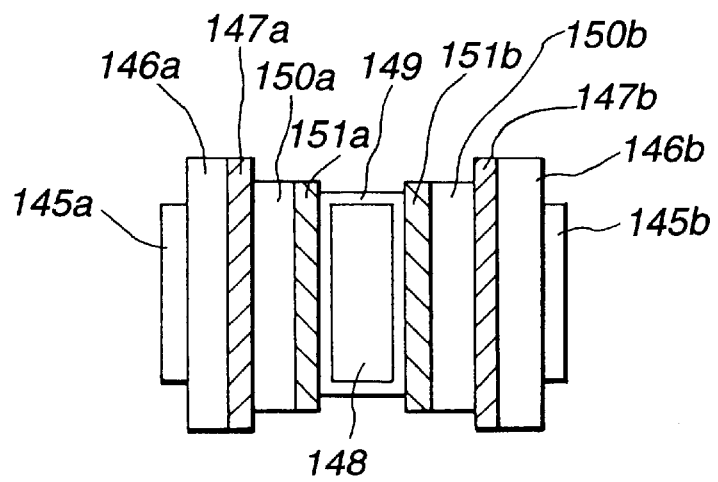
FIG. 13 is an explanatory diagram showing the outline structure of a liquid-crystal shutter having the capability of a diaphragm.

As shown in FIG. 12, when a diaphragm is not placed in the scope unit 131 shown in FIG. 5A or 5B, a liquid-crystal shutter 124A placed in the TV camera unit 130 is provided with the capability of a diaphragm in addition to the capability of a shutter. Specifically, as shown in FIG. 13, the liquid-crystal shutter 124A has basically the same structure as the liquid-crystal shutter 124 shown in FIG. 8. However, transparent substrates 150a and 150b, and transparent electrodes 151a and 151b located on the transparent substrates 150a and 150b are additionally mounted one by one on both the sides of the liquid-crystal layer 148.

As shown in FIGS. 14A and 14B, the transparent electrodes 147a and 147b located outside are used to control a diaphragm, and the transparent electrodes 151a and 151b located inside are used to control a shutter.

To be more specific, when a voltage is applied to the liquid-crystal shutter 124A, as shown in FIG. 15, if the polarizing directions permitted by the two polarizing plates 145a and 145b are matched in TN mode, the polarizing direction of light permitted by a portion of the liquid-crystal shutter to which the voltage is applied does not vary. This means that light is not intercepted by the portion. On the contrary, the polarizing direction permitted by a portion of the liquid-crystal shutter to which the voltage is not applied is turned 90°. Light is therefore intercepted. Consequently, when a constant voltage that is slightly lower than a threshold voltage is applied to electrode A and a pulsating voltage is applied to electrodes a1 and a2, portions of the liquid-crystal shutter in which electrode A and electrodes a1 and a2 overlap each other constitute a shutter.

Moreover, a liquid-crystal shutter 124B shown in FIG. 16A is designed to implement the capability of a diaphragm in the TV camera unit 130. As shown in FIG. 16B, the liquid-crystal shutter 124B is made by placing a first mechanical aperture plate 152 shown in FIG. 16C and a second aperture plate 153 shown in FIG. 16D on the front side of the liquid-crystal shutter 124. In the first aperture plate 152, for example, two sets of apertures 154a and 154b, and 155a and 155b are formed axially symmetrically. In the second aperture plate 153, apertures 153a and 153b are formed with a given diameter and spacing. The capability of a diaphragm given by the liquid-crystal shutter 124B is implemented by turning the first aperture plate 152 relative to the second aperture plate 153 that is stationary. Thus, aperture stops suitable for each scope unit can be selected.

Next, a means for disuniting a plurality of images having a parallax between them in a TV camera unit on the basis of polarization will be described.

As shown in FIG. 17A, a TV camera unit 156 of this embodiment has a polarizing plate 157 that consists of areas 157a and 157b permitting polarizing directions that are, as shown in FIG. 17B, mutually perpendicular. Light beams passing through the polarizing plate 157 and representing right and left images are recomposed into converged light by image formation lenses 125. The converged light is then split into light beams representing the right and left images by a polarization beam splitter 158, and formed on the imaging planes of imaging devices 105a and 105b located separately. Thus, a three-dimensional image can be discerned.

The other components are identical to those of the aforesaid embodiment. A scope unit 131 to be coupled with the TV camera unit 156 has the same configuration as any of those shown in FIG. 5. The shapes of the engagement sections of the TV camera units and scope unit 131 are identical to those shown in FIG. 5.

The polarizing plate 157 in the TV camera unit includes two areas 157a and 157b permitting mutually-perpendicular polarizing directions. The polarizing areas are arranged so that only one of two light beams being emitted from the scope unit 131 and passing through aperture stops (123a and 123b, 136a and 136b, or 140a and 140b) will be transmitted by one of the polarizing areas. A direction X in which the two aperture stops are separated from each other and a direction Y of a border between the two polarizing areas 157a and 157b of the polarizing plate are substantially orthogonal to each other.

FIG. 18A shows a variant of the embodiment shown in FIG. 17. A plurality of slit-type polarizing plates 159 which permit mutually-orthogonal polarizing directions are, as shown in FIG. 18C or 18D, mounted alternately on the front side of an imaging device 105 instead of the polarization beam splitter 158 to be included in the TV camera unit 156. Specifically, the two polarizing directions permitted by the slit-type polarizing plates 159 and the two polarizing directions permitted by the polarizing plate 157 agree with each other. Right and left images are formed alternately in a slit-like form on the imaging plane of the imaging device 105. Electric signals representing the right and left images formed on the imaging plane of the imaging device are processed and displayed separately, whereby a three-dimensional image can be discerned.

Figure 19:
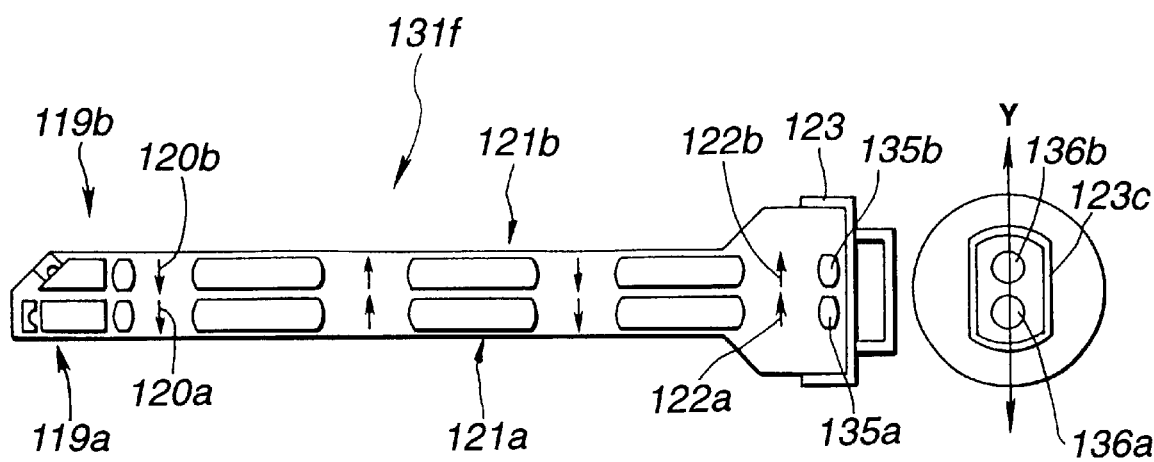
Figure 19:
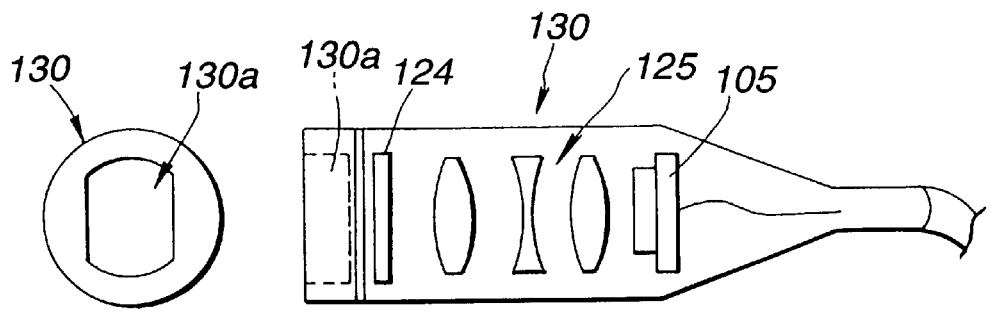
Figure 19:
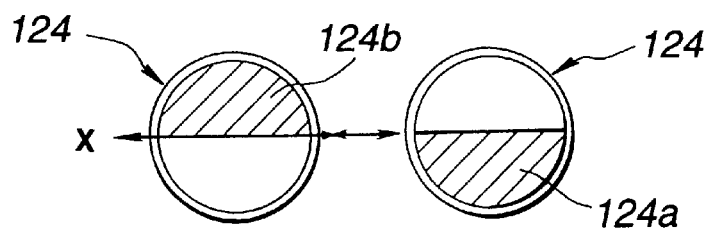

In FIGS. 19 and 20, two observation optical systems permitting different field-of-view directions are incorporated in one scope unit 131f or 131g. Even these scope units 131f and 131g have outer sections 123c of diaphragms 123 thereof shaped like those in the aforesaid embodiments so that the scope units can be coupled with a TV camera unit 130 of a stereoscopic endoscope system 101.

Specifically, as shown in FIG. 19A, this rigid scope has two observation optical systems permitting different field-of-view directions arranged in parallel in an insertion unit. In other words, last images 122a and 122b, which are entrance pupils of aperture stops 136a and 136b of the scope unit 131f, can be disunited on a temporal basis or on the basis of polarization and then picked up by means of the TV camera unit 130 shown in FIG. 19B.

By contrast, in FIG. 20A, two stereoscopic endoscope observation optical systems of a single-objective single-relay optical system type which permit different field-of-view directions are arranged in parallel. In other words, it is made possible that last images, which are entrance pupils of four aperture stops of the scope unit 131g; right and left aperture stops 123a and 123b associated with a direct-view direction and right and left aperture stops 123d and 123e associated an oblique-view direction, are disunited on a temporal basis or on the basis of polarization by means of a TV camera unit 130 shown in FIG. 20B.

Specifically, for disuniting the entrance pupils temporally, four areas 160a, 160b, 160c, and 160d as shown in FIG. 20 are regarded as entrance pupil separation areas. Right and left images emanating from the direct-view direction are acquired through the areas 160a and 160b, and right and left images emanating from the oblique-view direction are acquired through the areas 160c and 160d.

For disuniting the entrance pupils on the basis of polarization, a polarizing plate 161 is, as shown in FIG. 20D, placed in the TV camera unit 156 shown in FIG. 17. The polarizing plate 161 is used to specify the entrance pupils emanating from one of the field-of-view directions. Thereafter, a polarizing plate 157 and polarization beam splitter 158 are used to disunite the entrance pupils into light beams representing right and left images. The right and left images are formed on the imaging planes of imaging devices 105a and 105b located independently, whereby a three-dimensional image can be discerned. The polarizing plate 161 may be a mechanically rotatable plate or a plate that is formed using a liquid crystal or the like and designed to intercept light electrically.

For displaying images emanating from two field-of-view directions of the direct-view and oblique-view directions on a monitor, the images may be switched if necessary and displayed in a screen on one monitor. Alternatively, the screen on a monitor may be divided into a plurality of areas and the images may be displayed in the areas at a time. Otherwise, the images may be displayed separately on two monitors.

As described so far, according to the present invention, one image formation optical system is used to form a plurality of object images having a parallax between them on an imaging means. If an aperture stop of the image formation optical system is made sufficiently large, when scope units which are mutually different in a diameter of an aperture stop or a spacing between aperture stops are attached to one TV camera unit, observation can be achieved without obstruction of light beams.

To be more specific, the size of an aperture stop of an image formation optical system is set to agree with the largest diameter of an aperture stop or the largest spacing between aperture stops of all diameters or spacings provided by scope units employed. Thus, whichever one of the scope units is employed, emitted light can be utilized for image formation by the image formation optical system without a leakage.

Moreover, for sequentially picking up a plurality of images having a parallax between them, a shutter or the like should be included as a means for alternately switching transmission and interception on a time-sharing basis relative to different areas or halves of an aperture stop of an image formation optical system. A combination of polarizing filters may be included as a means for transmitting mutually-different polarized components relative to different areas of the aperture stop of the image formation optical system in place of the above means. Furthermore, a means for selectively transmitting the different polarized components may be placed on the incident side of an imaging device. In these cases, it is desired that the size of each aperture stop of a scope unit should substantially be agreed with that of the aperture stop of the image formation optical system. It is also desired that the switching means or the means for transmitting polarized light be placed at a position of image formation or in the vicinity of the position.

Furthermore, when a TV camera unit in accordance with this embodiment is employed in a rigid scope used for normal observation but not designed for stereoscopy, a means for producing a plurality of images having a parallax between them is not actuated. If the means is actuated, one of right and left images is not displayed. When it says that the means is not actuated, the following mode is conceivable: when a means for switching a plurality of images on a time-sharing basis is a means for switching passage and interception such as a shutter, the means is set in a full-surface transparent state. When an amount of light emitted from a scope unit is sufficiently large, the means may be retained in a partly-transparent state or partly-interceptive state.

One image formation optical system is employed in a TV camera unit in accordance with the present invention. An optical system for forming two images having a parallax between them is shared by right and left images. A variation of an image deriving from errors caused during manufacturing occurs in both the right and left images in the same manner. An error in magnification between the right and left images and a shift of a focal point are therefore small. Moreover, since the number of parts is small, assembling efficiency is better.

In the present invention, it will be apparent that a wide range of different embodiments can be formed on the basis of the invention without any departure from the spirit or scope of the invention. This invention will be limited to the appended claims but not restricted to any specific embodiments.

AVAILABILITY IN INDUSTRY

As described so far, according to the present invention, a stereoscopic endoscope system comprises a scope unit including at least one objective optical system, and a TV camera unit including one image formation optical system for imaging a light beam emanating from the scope unit, and an imaging device for picking up images passing through the image formation optical system. The scope unit and TV camera unit are detachable from each other, and an image disuniting means incorporated in the TV camera unit can disunite a plurality of images. A TV imaging system for an endoscope comprises a scope unit having an insertion unit and a TV camera unit that can be attached to the scope unit. The TV camera unit includes a single image formation optical system, a stop splitting member for temporally splitting an aperture stop of the image formation optical system, and an imaging device for photoelectrically transferring images formed by the image formation optical system, and can disunite a plurality of images by temporally switching a state, in which one of two areas constituting the aperture stop of the image formation optical system is transparent and the other area is interceptive, and a state in which the one of the two areas is interceptive and the other area is transparent.

What is claimed is:

1. An imaging system for an endoscope, comprising:

a scope unit including an elongated insertion unit insertable in a narrow region; and a TV camera unit, wherein said TV camera unit has a first mount portion for operably connecting said TV camera, in an alternative manner, to: (a) a stereoscopic scope unit, having a second mount portion, used for three-dimensional observation that has an elongated insertion unit insertable in a narrow region and that emits a plurality of light beams for stereoscopic observation, and (b) a two-dimensional scope unit, having a third mount portion, used for two-dimensional observation that has an elongated insertion unit insertable in a narrow region and that emits a single light beam, said first mount portion being operably connectable to said second and third mount portions for permitting said TV camera to operate with said stereoscopic scope unit and said two-dimensional scope unit, said stereoscopic scope unit includes an observation optical system having a single optical axis, said TV camera unit includes a single image formation optical system, a means for splitting an aperture stop of said image formation optical system, and a single imaging means for photoelectrically transforming images formed by said image formation optical system, said means for splitting an aperture stop transmits a first polarized light component of light entering one of two areas constituting said aperture stop of said image formation optical system, and transmits a second polarized light component, which is different from said first polarized light component, of light entering the other area, said TV camera unit includes a coupling section that can be mounted on said stereoscopic scope unit and two-dimensional scope unit, and said imaging means picks up light beams transmitted through said two areas, wherein said means for disuniting light beams is a composite polarizer made by juxtaposing numerous first polarizing devices for intercepting said second polarized light component and transmitting said first polarized light component and numerous second polarizing devices for intercepting said first polarized light component and transmitting said second polarized light component, and said composite polarizer is placed on the incident side of one imaging device, and wherein said first polarized light component and said second polarized light component are orthogonal to each other.

2. An imaging system for an endoscope, comprising:

a scope unit including an elongated insertion unit insertable in a narrow region; and a TV camera unit, wherein said TV camera unit has a first mount portion for operably connecting said TV camera, in an alternative manner, to: (a) a stereoscopic scope unit, having a second mount portion, used for three-dimensional observation that has an elongated insertion unit insertable in a narrow region and that emits a plurality of light beams for stereoscopic observation, and (b) a two-dimensional scope unit, having a third mount portion, used for two-dimensional observation that has an elongated insertion unit insertable in a narrow region and that emits a single light beam, said first mount portion being operably connectable to said second and third mount portions for permitting said TV camera to operate with said stereoscopic scope unit and said two-dimensional scope unit, said TV camera unit includes a single image formation optical system, a means for splitting an aperture stop of said image formation optical system, and an imaging means for photoelectrically transforming images formed by said image formation optical system;

said means for splitting an aperture stop transmits a first polarized light component of light entering one of two areas constituting said aperture stop of said image formation optical system, and transmits a second polarized light component, which is different from said first polarized light component, of light entering the other area; and said imaging means picks up light beams transmitted through said two areas, wherein said means for disuniting light beams is a composite polarizer made by juxtaposing numerous first polarizing devices for intercepting said second polarized light component and transmitting said first polarized light component and numerous second polarizing devices for intercepting said first polarized light component and transmitting said second polarized light component, and said composite polarizer is placed on the incident side of one imaging device, and wherein said first polarized light component and said second polarized light component are orthogonal to each other.

3. An imaging system for an endoscope, comprising:

a scope unit including an elongated insertion unit insertable in a narrow region; and a TV camera unit, wherein said TV camera unit has a first mount portion for operably connecting said TV camera, in an alternative manner, to: (a) a stereoscopic scope unit, having a second mount portion, used for three-dimensional observation that has an elongated insertion unit insertable in a narrow region and that emits a plurality of light beams for stereoscopic observation, and (b) a two-dimensional scope unit, having a third mount portion, used for two-dimensional observation that has an elongated insertion unit insertable in a narrow region and that emits a single light beam, said first mount portion being operably connectable to said second and third mount portions for permitting said TV camera to operate with said stereoscopic scope unit and said two-dimensional scope unit, said TV camera unit includes a single image formation optical system, a means for splitting an aperture stop of said image formation optical system, and an imaging means for photoelectrically transforming images formed by said image formation optical system;

said means for splitting an aperture stop transmits a first polarized light component of light entering one of two areas constituting said aperture stop of said image formation optical system, and transmits a second polarized light component, which is different from said first polarized light component, of light entering the other area; and said imaging means picks up light beams transmitted through said two areas, wherein said first polarized light component and said second polarized light are arranged in the vicinity of the aperture stops in said scope unit.

4. An imaging system for an endoscope comprising:

a scope unit including at least one objective optical system located in an elongated insertion unit insertable in a narrow region and at least one conveying optical system for conveying an object image;

a TV camera unit including:
   one image formation optical system for imaging a light beam emitted from said scope unit, and
   an imaging means for picking up images passing through said image formation optical system; and an image disuniting means for disuniting a plurality of images, said image disuniting means including an image shutter element arranged in said TV camera unit;

characterized in that
   said scope unit and TV camera unit are freely detachable to each other;
   said image disuniting means further comprises a diaphragm located in said scope unit or TV camera unit, said diaphragm having a plurality of apertures or a plurality of aperture stops;
   wherein said image shutter element
      in a first mode of operation for stereoscopic imaging is disuniting images passed through said diaphragm on a temporal basis, and
      in a second mode of operation is set in a full-surface transparent state, a partly-transparent state or a partly interceptive state.

5. Imaging system according to claim 4, wherein said scope unit and said TV camera unit are freely attachable to each other by engaging a scope joint formed in said TV camera unit with an outer section of said diaphragm located on said scope unit.

6. Imaging system according to claim 4, wherein said image disuniting means is a means for disuniting images on the basis of polarization.

7. Imaging system according to claim 4, wherein a plurality of scope units which are attachable to said TV camera unit are mutually different in terms of at least one of an angle of field, a diameter of an aperture stop, a spacing between aperture stops, and a type of stereoscopic endoscope optical system.

8. Imaging system according to claim 4, wherein said shutter element is a liquid-crystal shutter.

9. Imaging system according to claim 8, wherein said liquid-crystal shutter is a field-effect liquid-crystal shutter.

10. Imaging system according to claim 8 or 9, wherein said shutter element further provides the capability of said diaphragm.

11. Imaging system according to claim 4, wherein said image formation optical system in said TV camera unit is a zoom lens.

12. Imaging system according to claim 4, wherein said shutter element is a means having the ability to change a spectral characteristic such as laser beam cut off ability, infrared cutoff ability or color correction ability.

13. Imaging system according to claim 4 or 5, wherein said scope unit and TV camera unit are turnable relative to each other with the longitudinal directions thereof as axes.

14. Imaging system according to claim 4 or 5, wherein coupling sections of scope units freely attachable to said TV camera unit have the same shape.

15. Use of a single TV camera unit for either a stereo endoscopic application or a normal endoscopic observation application (2-Dim), said TV camera unit is freely detachable to a plurality of scope units, each scope unit including at least one objective optical system located in an elongated insertion unit insertable in a narrow region and at least one conveying optical system for conveying an object image; and said camera unit including:

an image formation optical system for imaging a light beam emitted from said attached scope unit, an imaging means for picking up images passing through said image formation optical system, and an image shutter element;

wherein in said stereo endoscopic application said scope unit comprises a diaphragm having a plurality of apertures or a plurality of aperture stops or said TV camera unit comprises a diaphragm having a plurality of apertures, wherein said image shutter element is disuniting images passed through said diaphragm on a temporal basis, and wherein in said normal operation application said image shutter element is set in a full-surface transparent state, a partly-transparent state or a partly-interceptive state.

* * * * *